(12) United States Patent
Jester et al.

(10) Patent No.: US 11,024,418 B2
(45) Date of Patent: Jun. 1, 2021

(54) SYSTEMS AND METHODS FOR INTELLIGENT RADIOLOGY WORK ALLOCATION

(71) Applicant: General Electric Company, Schenectady, NY (US)

(72) Inventors: Eric Jester, Hoffman Estates, IL (US); Arun Viswanath, Lake Zurich, IL (US); Madhu Seepani, Lake In The Hills, IL (US); Shaoyu Feigler, Barrington, IL (US); Jeff Chu, Buffalo Grove, IL (US); Jiaohuan Wang, Schaumburg, IL (US); Vineet Ahuja, Palatine, IL (US); Brittany Melissa Johnson, Chicago, IL (US); Charlotte Mae Shelton, Gilbert, AZ (US); Rhonda Eckstein, Baileyton, AL (US)

(73) Assignee: General Electric Company, Schenectady, NY (US)

( * ) Notice: Subject to any disclaimer, the term of this patent is extended or adjusted under 35 U.S.C. 154(b) by 892 days.

(21) Appl. No.: 15/692,452

(22) Filed: Aug. 31, 2017

(65) Prior Publication Data
US 2017/0364645 A1 Dec. 21, 2017

Related U.S. Application Data

(63) Continuation of application No. 14/091,769, filed on Nov. 27, 2013, now abandoned.

(51) Int. Cl.
*G16H 40/20* (2018.01)
*G06F 3/0484* (2013.01)
*G16H 30/20* (2018.01)

(52) U.S. Cl.
CPC ......... *G16H 40/20* (2018.01); *G06F 3/04842* (2013.01); *G16H 30/20* (2018.01)

(58) Field of Classification Search
None
See application file for complete search history.

(56) References Cited

U.S. PATENT DOCUMENTS 7,970,634 B2   6/2011   Backhaus et al.
9,558,323 B2   1/2017   Jester et al.
(Continued)

OTHER PUBLICATIONS

United States Patent and Trademark Office, "Non-final Office Action," issued in connection with U.S. Appl. No. 14/091,801, dated Feb. 1, 2017, 61 pages.

(Continued)

*Primary Examiner* — Rachelle L Reichert

(57) ABSTRACT

An example system to distribute a medical exam to an examiner includes a first interface to display a medical exam identifier associated with a medical exam stored in a patient record database and an examiner availability indicator to be displayed via the first interface. The examiner availability indicator is to be updated via a second interface. The example system includes an exam allocator to automatically allocate the medical exam to the examiner and an assignment tool to be displayed to a user via the first interface and to facilitate assignment of the allocated exam to the examiner. At least one of the exam allocator or the assignment tool is to be communicatively associated with the examiner availability indicator. Upon assignment of the medical exam to the examiner, the medical exam identifier is displayed in an examiner work queue via the first interface, the second interface, and a third interface.

17 Claims, 10 Drawing Sheets

(56) References Cited

U.S. PATENT DOCUMENTS

| | | | |
|---|---|---|---|
| 9,817,945 | B2 | 11/2017 | Jester et al. |
| 2003/0149598 | A1 | 8/2003 | Santoso et al. |
| 2004/0019501 | A1 | 1/2004 | White et al. |
| 2004/0249676 | A1 | 12/2004 | Marshall et al. |
| 2006/0053035 | A1 | 3/2006 | Eisenberg |
| 2006/0143060 | A1 | 6/2006 | Conry et al. |
| 2006/0195339 | A1* | 8/2006 | Backhaus ............... G16H 40/20 705/2 |
| 2006/0212317 | A1 | 9/2006 | Hahn et al. |
| 2007/0073556 | A1* | 3/2007 | Lau ........................ G16H 40/20 705/2 |
| 2007/0143136 | A1 | 6/2007 | Moore, III et al. |
| 2007/0179831 | A1 | 8/2007 | Patnaik et al. |
| 2007/0226008 | A1 | 9/2007 | Halsted et al. |
| 2009/0240529 | A1 | 9/2009 | Chess et al. |
| 2009/0287500 | A1 | 11/2009 | Benjamin et al. |
| 2009/0313046 | A1 | 12/2009 | Badgett et al. |
| 2011/0066449 | A1 | 3/2011 | Backhaus et al. |
| 2011/0113329 | A1 | 5/2011 | Pusateri |
| 2011/0125539 | A1 | 5/2011 | Bollapragada et al. |
| 2012/0096385 | A1 | 4/2012 | Bank et al. |
| 2012/0116816 | A1 | 5/2012 | Smith |
| 2012/0226719 | A1 | 9/2012 | Sewall |
| 2013/0018674 | A1 | 1/2013 | Bedi et al. |
| 2013/0132105 | A1 | 5/2013 | Wood-Salomon et al. |
| 2013/0132142 | A1* | 5/2013 | Wood-Salomon ..... G06Q 10/10 705/7.15 |
| 2013/0151284 | A1 | 6/2013 | Cohen-Solal et al. |
| 2013/0218592 | A1 | 8/2013 | Hashmat |
| 2013/0262132 | A1* | 10/2013 | Sant .................... G06F 19/3418 705/2 |
| 2015/0066529 | A1 | 3/2015 | Lattuca et al. |
| 2015/0149192 | A1 | 5/2015 | Jester et al. |
| 2015/0149193 | A1 | 5/2015 | Jester et al. |
| 2015/0149206 | A1 | 5/2015 | Jester et al. |
| 2017/0091399 | A1 | 3/2017 | Jester et al. |

OTHER PUBLICATIONS

United States Patent and Trademark Office, "Final Office Action," issued in connection with U.S. Appl. No. 14/091,801, dated Sep. 9, 2016, 22 pages.

United States Patent and Trademark Office, "Notice of Allowance," issued in connection with U.S. Appl. No. 14/091,812, dated Sep. 12, 2016, 32 pages.

United States Patent and Trademark Office, "Advisory Action," issued in connection with U.S. Appl. No. 14/091,812, dated Jul. 6, 2016, 4 pages.

United States Patent and Trademark Office, "Non-final Office Action," issued in connection with U.S. Appl. No. 14/091,801, dated Feb. 18, 2016, 22 pages.

United States Patent and Trademark Office, "Final Office Action," issued in connection with U.S. Appl. No. 14/091,801, dated Apr. 27, 2016, 26 pages.

United States Patent and Trademark Office, "Non-final Office Action," issued in connection with U.S. Appl. No. 14/091,812, dated Oct. 23, 2015, 24 pages.

Burke et al., "The State of the Art of Nurse Rostering," Journal of Scheduling, 2004, pp. 441-499, vol. 7, Kluwer Academic Publishers, the Netherlands, 59 pages.

Dang et al., "An ontological knowledge framework for adaptive medical workflow," Journal of Biomedical Informatics, 2008, pp. 829-836, vol. 41, Knowledge Management, Siemens Corporate Research, Princeton, NJ, 8 pages.

Mack et al., "New Aspects of Image Distribution and Workflow in Radiology," Journal of Digital Imaging, May 2000, pp. 17-21, vol. 13 No. 2, W.B. Saunders Company, Witten, Germany, 5 pages.

Meyer et al., "A Database Program for the Management of Staff Scheduling in a Radiology Department," Presented at the annual meeting of the Society for Pediatric Radiology, St Louis, May 1997, American Journal of Roentgenology, pp. 1489-1492, vol. 169 (Dec. 1997), American Roentgen Ray Society, 4 pages.

Naidu et al., "Managing Personnel through Staff Scheduling Algorithms," Proceedings of the Fifth Joint Conference on Information Sciences, 2000, pp. 829-835, vol. 5 No. 2, Duke University, Durham, NC, 7 pages.

Welter et al., "Workflow management of content-based image retrieval for CAD support in PACS environments based on IHE," International Journal for Computer Assisted Radiology and Surgery, published Apr. 9, 2010, pp. 393-400, vol. 5, Aachen University Hospital, Aachen, Germany, 8 pages.

United States Patent and Trademark Office, "Advisory Action," issued in connection with U.S. Appl. No. 14/091,769, dated Aug. 3, 2017, 5 pages.

United States Patent and Trademark Office, "Final Office Action," issued in connection with U.S. Appl. No. 14/091,769, dated May 19, 2017, 21 pages.

United States Patent and Trademark Office, "Non-final Office Action," issued in connection with U.S. Appl. No. 14/091,769, dated Oct. 14, 2016, 21 pages.

United States Patent and Trademark Office, "Advisory Action," issued in connection with U.S. Appl. No. 14/091,769, dated Jul. 29, 2016, 14 pages.

United States Patent and Trademark Office, "Final Office Action," issued in connection with U.S. Appl. No. 14/091,769, dated May 9, 2016, 16 pages.

United States Patent and Trademark Office, "Non-final Office Action," issued in connection with U.S. Appl. No. 14/091,769, dated Aug. 31, 2015, 23pages.

United States Patent and Trademark Office, "Notice of Allowance," issued in connection with U.S. Appl. No. 14/091,801, dated Jul. 28, 2017, 28 pages.

* cited by examiner

SYSTEMS AND METHODS FOR INTELLIGENT RADIOLOGY WORK ALLOCATION

RELATED APPLICATIONS

This patent arises as a continuation of U.S. patent application Ser. No. 14/091,769, entitled "Systems and Methods for Intelligent Radiology Work Allocation," filed Nov. 27, 2013. U.S. patent application Ser. No. 14/091,769 is hereby incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medication orders, medical histories, imaging data, test results, diagnosis information, management information, and/or scheduling information, for example.

Medical exam results stored in, for example, the radiology information system, require review by an examining radiologist. Distribution of the exams for review by the radiologist involves consideration of various factors, including, for example, radiologist workload, exam characteristics, and/or hospital efficiency goals. Such considerations are often present across a network of radiologists and/or hospitals. Efforts to balance radiologist workloads and availability with exams requiring review and institutional work flow goals are time-consuming, inefficient, and result in inequities in distribution of the medical exams for review. Further, radiologists lack efficient tools for managing workflows in view of radiologist availability, specialty, and/or the workloads and availability of other radiologists within a network.

BRIEF SUMMARY

Certain examples provide methods, systems, and machine readable storage devices or storage discs for medical exam distribution. Certain examples provide a system to distribute a medical exam to an examiner. The example system includes a first interface to display a medical exam identifier associated with a medical exam stored in a patient record database and an examiner availability indicator to be displayed via the first interface. The examiner availability indicator is to be updated via a second interface. The second interface to be viewed by the examiner. The example system includes an exam allocator to automatically allocate the medical exam to the examiner. The example system includes an assignment tool to be displayed to a user via the first interface. The assignment tool is to facilitate assignment of the allocated exam to the examiner. In the example system, at least one of the exam allocator or the assignment tool is to be communicatively associated with the examiner availability indicator. The example system includes an examiner work queue. In the example system, upon assignment of the medical exam to the examiner, the medical exam identifier is displayed in the examiner work queue via the first interface, the second interface, and a third interface. In the example system, the third interface is to be viewed by a second examiner.

Certain examples provide a method for distributing a medical exam to an examiner. The example method includes retrieving a medical exam identifier associated with a medical exam stored in a patient record database. The method includes processing an examiner availability indicator. In the example method, the examiner availability indicator is updated via a first interface. The example method includes displaying the medical exam identifier and the examiner availability indicator via a second interface. The example method also includes allocating the medical exam to the examiner. The example method includes facilitating an assignment of the allocated exam to the examiner via the second interface. In the example method, at least one of allocating the medical exam or facilitating the assignment of the allocated medical exam is based on the examiner availability indicator. The example method also includes displaying the medical exam identifier in an examiner work queue upon assignment via the first interface, the second interface, and a third interface. In the example method, the third interface is to be viewed by a second examiner.

Certain examples provide a machine readable storage device or storage disc storing instruction thereon, which, when read, cause a machine to at least retrieve a medical exam identifier associated with a medical exam stored in a patient record database. The example instructions cause the machine to at least process an examiner availability indicator. The examiner availability indicator is updated via a first interface. The example instructions cause the machine to at least display the medical exam identifier and the examiner availability indicator via a second interface. The example instructions also cause the machine to at least allocate the medical exam to the examiner. The example instructions cause the machine to at least facilitate assignment of the allocated medical exam to the examiner via the second interface. At least one of the allocation or the assignment is based on the examiner availability indicator. The example instructions also cause the machine to at least display the medical exam identifier in an examiner work queue upon assignment via the first interface, the second interface, and a third interface. The third interface to be viewed by a second examiner.

BRIEF DESCRIPTION OF SEVERAL VIEWS OF THE DRAWINGS

FIG. 5 illustrates a third example screen of the example graphical user interface associated with the example medical exam distributor of FIG. 1.

FIG. 6 illustrates a fourth example screen of the example graphical user interface associated with the example medical exam distributor of FIG. 1.

Figure 1:
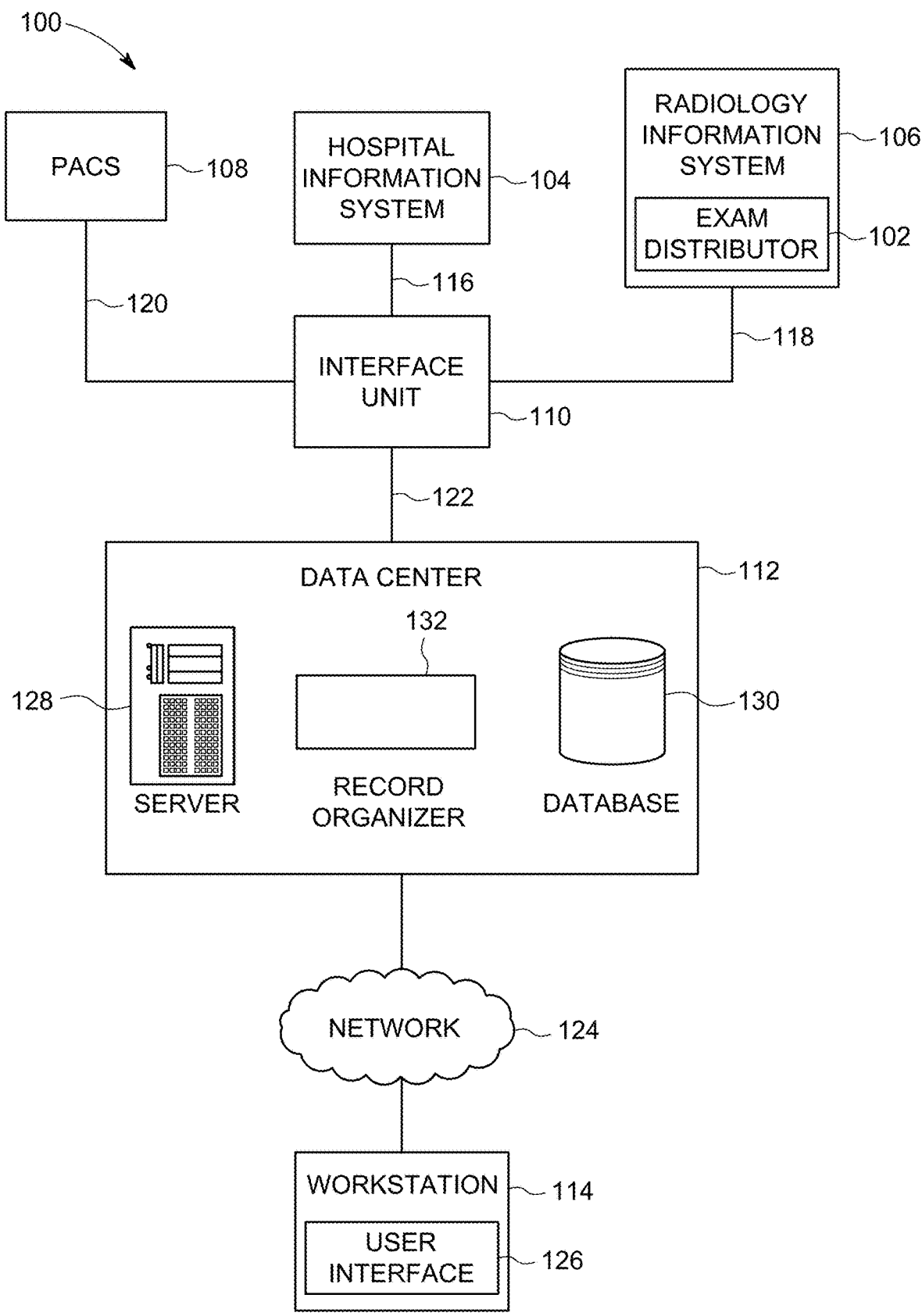
FIG. 1 is a block diagram of an example medical exam distributor in an example healthcare system.

The foregoing summary, as well as the following detailed description of certain examples of the present disclosure, will be better understood when read in conjunction with the appended drawings. For the purpose of illustrating the disclosure, certain examples are shown in the drawings. It should be understood, however, that the present disclosure is not limited to the arrangements and instrumentality shown in the attached drawings.

DETAILED DESCRIPTION OF CERTAIN EXAMPLES

Although the following discloses example methods, systems, and machine readable storage devices and storage discs including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, and machine readable storage devices and storage discs, the examples provided are not the only way to implement such methods, systems, and machine readable storage devices and storage discs.

Also, although the methods, systems and machine readable storage mediums disclosed here are described in regards to healthcare applications, including, but not limited to, radiology information systems, it is to be understood that the present methods, systems and machine readable storage mediums may also be used to distribute information in any other industry/application.

A medical exam conducted on patient requires review by a healthcare practitioner for purposes of obtaining, for example, diagnostic information from the exam. In a hospital setting, medical exams may be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, consider the exam attributes as well as staff availability, staff credentials, and/or institutional factors such as service level agreements and/or overhead costs. Balancing practitioner workloads in view of the exams requiring review involves time-consuming efforts that result in inefficiencies and/or inequities in exam distribution across a network of practitioners. Further, practitioners may habitually decline to review and/or select to review exams having certain attributes. Load-balancing rules that automatically allocate exams to practitioners while allowing for a user, such as an administrator and/or a practitioner, to review the allocation and control assignment of the exams provide for optimization in practitioner workloads in view of hospital workflow goals and clinical targets.

Additionally, a practitioner may wish to manage his workload, which may include one or more exams for review. For example, a practitioner may wish to designate select times or capacities in which the practitioner is available and/or unavailable to review exams. In some examples, the practitioner may wish to manage exams distributed to his workload based on practitioner specialty and/or exam attributes. A system that allows the practitioner to create one or more profiles defining radiologist-specific criteria and that distributes exams based on the profiles provides for a practitioner-centered workflow system. Further, in responding to profile criteria defined by practitioners across a network, such a system provides for a dynamic, load-balancing approach to exam distribution and shared workload management.

Disclosed herein are example systems, methods, and machine readable storage devices and storage discs that provide for workload distribution of medical exams to examining practitioners. The disclosed example systems, methods, and machine readable storage devices and storage discs can be used as part of a radiology information system to distribute radiology medical exams to radiologists for review. The examples disclosed herein include graphical user interfaces accessible by one or more examining radiologists and/or administrators.

The disclosed example graphical user interfaces facilitate management of the radiologist's work queue by providing for the radiologist to define availability, workload, and/or specialty parameters via the graphical user interfaces. For example, a first radiologist can create profiles based on availability, specialty, and/or other parameters associated with a capacity in which the first radiologist performs at particular times and/or days of the week. In distributing exams to the first radiologist, load-balancing rules distribute exams to the first radiologist based on one or more criteria associated with a profile. The first radiologist can view the distributed exams associated with a particular profile via the example graphical user interfaces. The example graphical user interfaces facilitate review of the automatic allocation of a medical exam to the first radiologist based on the load-balancing rules. In some examples, the disclosed examples enable acceptance or rejection by the first radiologist of a distributed exam as part of the first radiologist's work queue. In further examples, an administrator can confirm allocation of a medical exam to the radiologist by assigning the exam to the first radiologist.

The examples disclosed herein also facilitate assignment of an exam to a second radiologist based on availability, workload, and/or specialty of at least one of the first radiologist and/or the second radiologist, as well as in view of exam attributes. For example, the load-balancing rules dynamically respond to the availability and/or unavailability of the first radiologist by distributing exams to the second radiologist and/or other radiologists in the network. Also, in the disclosed examples, the workload of the first radiologist as well as parameters such as the availability of the first radiologist are shared with the second radiologist via the example graphical user interfaces to promote collaboration and consultation among the network of radiologists reviewing exams. In the disclosed examples, information concerning radiologist availability, workload, and/or exam attributes is dynamically updated and shared via interfaces accessible by radiologists and/or administrators to provide for communicative approach to exam distribution and workflow management.

The examples disclosed herein also facilitate real-time review of exams by automatically allocating an exam to a radiologist for substantially immediate review of the exam. In such examples, rather than the exam being assigned to the examiner work queue for review at a later time, the exam is distributed for immediate review and reporting by the radiologist via an exam review and reporting screen (e.g., an exam reading tool). The radiologist can selectively enable the auto-serving of exams or the distribution of exams to the work queue based on, for example, the radiologist's availability. Thus, the disclosed examples accommodate various approaches to exam distribution and review to increase workflow management and efficiency.

Turning now to the figures, FIG. 1 shows a block diagram of an example healthcare system 100 capable of implementing an example medical exam distributor 102. The example healthcare system 100 includes the example medical exam distributor 102, a hospital information system (HIS) 104, a radiology information system (RIS) 106, a picture archiving and communication system (PACS) 108, an interface unit 110, a data center 112, and a workstation 114. In the illustrated example, the HIS 104, the RIS 106, and the PACS 108 are housed in a healthcare facility and locally archived. However, in other implementations, the HIS 104, the RIS 106, and/or the PACS 108 can be housed one or more other suitable locations. In certain implementations, one or more of the PACS 108, RIS 106, HIS 104, etc., can be implemented remotely via a thin client and/or downloadable software solution. Furthermore, one or more components of the healthcare system 100 can be combined and/or implemented together. For example, the RIS 106 and/or the PACS 108 can be integrated with the HIS 104; the PACS 108 can be integrated with the RIS 106; and/or the three example information systems 104, 106, and/or 108 can be integrated together. In other example implementations, the healthcare system 100 includes a subset of the illustrated information systems 104, 106, and/or 108. For example, the healthcare system 100 can include only one or two of the HIS 104, the RIS 106, and/or the PACS 108. Information (e.g., scheduling, test results, exam image data, observations, diagnosis, etc.) can be entered into the HIS 104, the RIS 106, and/or the PACS 108 by healthcare practitioners (e.g., radiologists, physicians, and/or technicians) before and/or after patient examination.

The HIS 104 stores medical information such as clinical reports, patient information, and/or administrative information received from, for example, personnel at a hospital, clinic, and/or a physician's office. The RIS 106 stores information such as, for example, radiology reports, radiology exam image data, messages, warnings, alerts, patient scheduling information, patient demographic data, patient tracking information, and/or physician and patient status monitors. Additionally, the RIS 106 enables exam order entry (e.g., ordering an x-ray of a patient) and image and film tracking (e.g., tracking identities of one or more people that have checked out a film). In some examples, information in the RIS 106 is formatted according to the HL-7 (Health Level Seven) clinical communication protocol. In certain examples, the medical exam distributor 102 is located in the RIS 106 to facilitate distribution of radiology exams to a radiologist workload for review. In an alternative example, the exam distributor 102 can be located separately or can be included in any other suitable device of the healthcare system 100.

The PACS 108 stores medical images (e.g., x-rays, scans, three-dimensional renderings, etc.) as, for example, digital images in a database or registry. In some examples, the medical images are stored in the PACS 108 using the Digital Imaging and Communications in Medicine ("DICOM") format. Images are stored in the PACS 108 by healthcare practitioners (e.g., imaging technicians, physicians, radiologists) after a medical imaging of a patient and/or are automatically transmitted from medical imaging devices to the PACS 108 for storage. In some examples, the PACS 108 can also include a display device and/or viewing workstation to enable a healthcare practitioner or provider to communicate with the PACS 108.

The interface unit 110 includes a hospital information system interface connection 116, a radiology information system interface connection 118, a PACS interface connection 120, and a data center interface connection 122. The interface unit 110 facilities communication among the HIS 104, the RIS 106, the PACS 108, and/or the data center 112. The interface connections 116, 118, 120, and 122 can be implemented by, for example, a Wide Area Network ("WAN") such as a private network or the Internet. Accordingly, the interface unit 110 includes one or more communication components such as, for example, an Ethernet device, an asynchronous transfer mode ("ATM") device, an 802.11 device, a DSL modem, a cable modem, a cellular modem, etc. In turn, the data center 112 communicates with the workstation 114, via a network 124, implemented at a plurality of locations (e.g., a hospital, clinic, doctor's office, other medical office, or terminal, etc.). The network 124 is implemented by, for example, the Internet, an intranet, a private network, a wired or wireless Local Area Network, and/or a wired or wireless Wide Area Network. In some examples, the interface unit 110 also includes a broker (e.g., a Mitra Imaging's PACS Broker) to allow medical information and medical images to be transmitted together and stored together.

The interface unit 110 receives images, medical reports, administrative information, exam workload distribution information, and/or other clinical information from the information systems 104, 106, 108 via the interface connections 116, 118, 120. If necessary (e.g., when different formats of the received information are incompatible), the interface unit 110 translates or reformats (e.g., into Structured Query Language ("SQL") or standard text) the medical information, such as medical reports, to be properly stored at the data center 112. The reformatted medical information can be transmitted using a transmission protocol to enable different medical information to share common identification elements, such as a patient name or social security number. Next, the interface unit 110 transmits the medical information to the data center 112 via the data center interface connection 122. Finally, medical information is stored in the data center 112 in, for example, the DICOM format, which enables medical images and corresponding medical information to be transmitted and stored together.

The medical information is later viewable and easily retrievable at the workstation 114 (e.g., by their common identification element, such as a patient name or record number). The workstation 114 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 114 receives commands and/or other input from a user via, for example, a keyboard, mouse, track ball, microphone, etc. The workstation 114 is capable of implementing a user interface 126 to enable a healthcare practitioner to interact with the healthcare system 100. For example, in response to a request from a physician, the user interface 126 presents a patient medical history. In other examples, a radiologist can retrieve and manage a workload of exams distributed for review to the radiologist by the medical exam distributor 102 via the user interface 126. In further examples, the radiologist can review the exam image data associated with the exams distributed by the exam distributor 102 via the user interface 126.

The example data center 112 of FIG. 1 is an archive to store information such as, for example, images, data, medical reports, and/or, more generally, patient medical records. In addition, the data center 112 can also serve as a central conduit to information located at other sources such as, for example, local archives, hospital information systems/radiology information systems (e.g., the HIS 104 and/or the RIS 106), or medical imaging/storage systems (e.g., the PACS 108 and/or connected imaging modalities). That is, the data center 112 can store links or indicators (e.g., identification numbers, patient names, or record numbers) to information. In the illustrated example, the data center 112 is managed by an application server provider ("ASP") and is located in a centralized location that can be accessed by a plurality of systems and facilities (e.g., hospitals, clinics, doctor's offices, other medical offices, and/or terminals). In some examples, the data center 112 can be spatially distant from the HIS 104, the RIS 106, and/or the PACS 108 (e.g., at General Electric® headquarters).

The example data center 112 of FIG. 1 includes a server 128, a database 130, and a record organizer 132. The server 128 receives, processes, and conveys information to and from the components of the healthcare system 100. The database 130 stores the medical information described herein and provides access thereto. The example record organizer 132 of FIG. 1 manages patient medical histories, for example. The record organizer 132 can also assist in procedure scheduling, for example.

The example medical exam distributor 102 identifies a medical exam needing review and facilitates distribution of the exam to an examiner, such as a radiologist. The medical exam can be stored in the data center 112 or located in any other component of the healthcare system 100. In some examples, the exam distributor 102 distributes one or more exams to a radiologist using pre-defined load-balancing rules based on one or more characteristics associated with an exam, an examiner, a network of examiners, and/or healthcare administrators. For example, as part of the RIS 106, the exam distributor 102 provides for the creation of one or more radiologist profiles via, for example, the user interface 126. A radiologist profile defines, for example, a radiologist's availability, specialty, preferred exam attributes, and/or other parameters associated with radiologist's workload. The exam distributor 102 considers the radiologist's profile in distributing radiology exams to the radiologist as well as to other radiologists associated with the RIS 106. For example, a first exam can be distributed by the medical exam distributor 102 to a first radiologist based on a specialty profile of the first radiologist, whereas a second exam can be distributed to a second examiner based on the second examiner's availability in view of a priority level of the exam. Further, one or more of the radiologist profile parameters, such as the radiologist's availability, can be viewed by other radiologists and/or users within the RIS 106 via the user interface 126 at respective workstations 114.

An identifier associated with the medical exam distributed by the medical exam distributor 102 can be viewed by, for example, the radiologist to whom the exam has been distributed, other radiologists associated with the RIS 106, and/or a hospital administrator, via a viewer, such as the user interface 126 of the workstation 114. While the exam distributor 102 can automatically distribute the exam to a radiologist, the exam distributor 102 can also receive user inputs via the user interface 126 related to confirmation and/or rejection of the automatic allocation of the exam to the radiologist. The medical exam distributor 102 dynamically responds to user inputs related to, for example, allocation of exams, creation/modification of radiologist profiles, and/or other user interaction via the user interface 126 to efficiently distribute exams to a reviewing radiologist's workflow in view of exam attributes. The exam distributor 102 further facilitates dynamic sharing of exam distribution statuses and/or radiologist characteristics, such as availability, among users associated with the RIS 106 to provide for a shared workflow management system.

Figure 2:
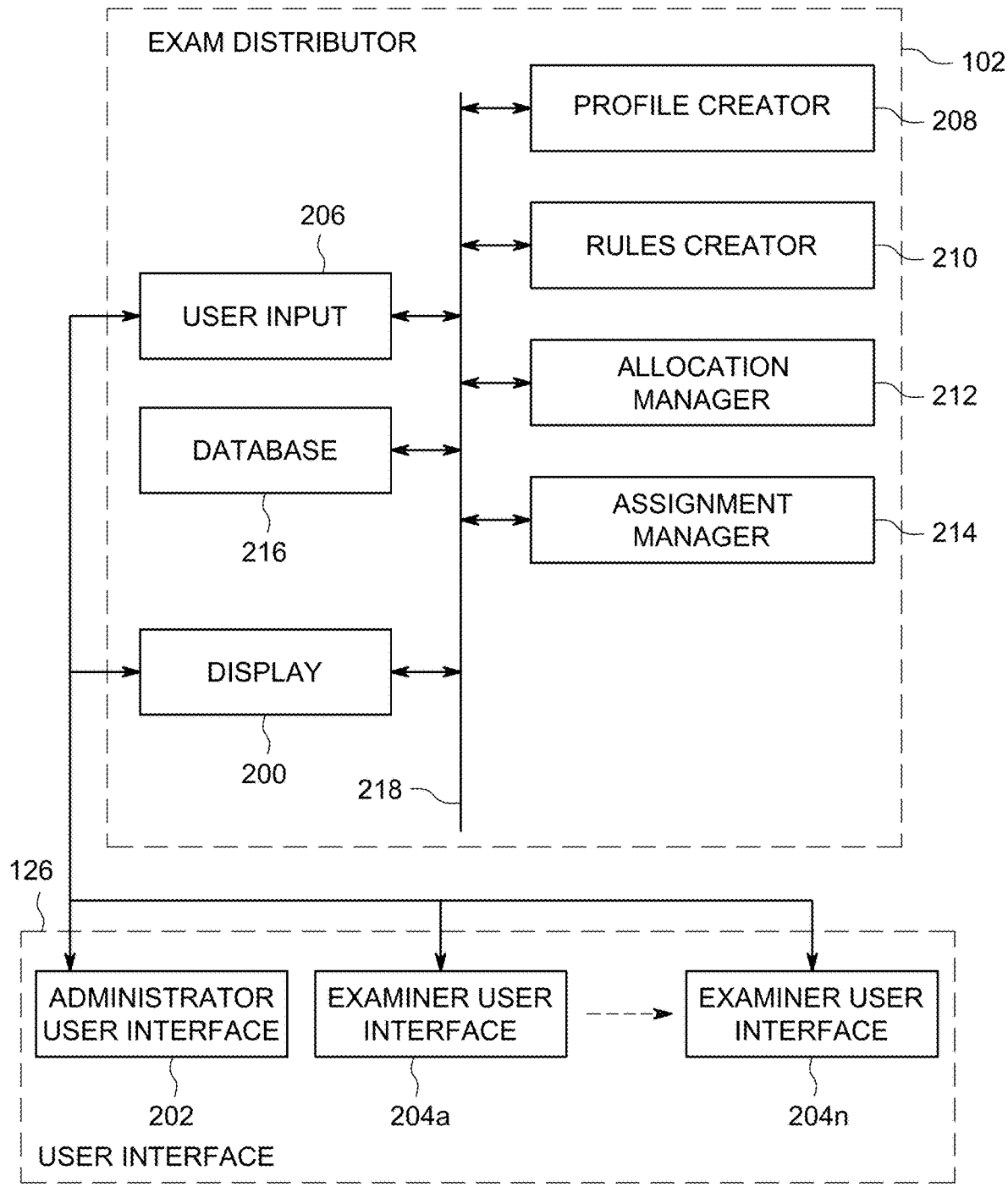
FIG. 2 is a block diagram of the example medical exam distributor of FIG. 1.

FIG. 2 shows a block diagram of the exam distributor 102 of FIG. 1. For example, the exam distributor 102 can be associated with the radiology information system of FIG. 1. The exam distributor 102 includes a display module 200, which may, for example, interact with the user interface 126 of the system 100 of FIG. 1. As will be described below (FIGS. 3-7), in some examples, the user interface 126 is an administrator user interface 202 accessible by, for example, a hospital or radiology department administrator. In further examples, the user interface 126 is an examiner user interface 204a-n accessible by one or more radiologists. The display module 200 can connect to any computer screen, image viewer and/or other display device known to those skilled in the art. The example exam distributor 102 also includes a user input module 206 for receiving, for example, a user input from one or more of the administrator interface 202 and/or the examiner user interfaces 204a-n.

The example exam distributor 102 also includes a profile creator 208. The profile creator 208 provides for the creation and/or modification of one or more radiologist profiles by a radiologist via the user input module 206. Profiles created via the profile creator 208 define, for example, a radiologist's specialty, availability, preferred exam attributes, workload capacity, and/or other characteristics associated with the radiologist at select times or on certain days of the week. A radiologist can select a profile via, for example, the examiner user interface 204a, which defines the radiologist's capacity to receive exams for review. In distributing exams for review, the exam distributor 102 at least partially considers the availability and/or workload of a radiologist based on one or more profiles when allocating and/or assigning an exam to the radiologist.

The example exam distributor 102 includes a rules creator 210. The rules creator 210 defines one or more rules used in automatically allocating an exam to a radiologist. In some examples, an administrator define, for examples, one or more departmental and/or institutional rules via the administrator user interface 202 and the user input module 206. Also, in some examples, the rules creator 210 creates rules based on radiologist profiles created by the profile creator 208. In other examples, the rules creator 210 defines one or more load-balancing rules based on, for example, radiologist workload thresholds, radiologist specialties, preferred radiologists, exam priority levels, and/or exam difficulty levels. In implementing the rules creator 210, the example exam distributor 102 optimizes distribution of an exam to a radiologist based a combination of rules associated with a radiologist profile, one or more exam attributes, and/or healthcare administration to match an exam with a reviewing radiologist. Also, in some examples where the exam distributor 102 is implemented across two or more institutions, the rules creator 102 performs a mapping of identifiers associated with the exams and/or the healthcare institutions to standardize exam distribution between institutions. For example, factors such as exam modality, body part, radiologist specialty, and/or institution location are considered by the rules creator as part of defining load-balancing rules. Such mapping across affiliated institutions provides for consistency in applying the load-balancing rules and benchmarks for comparing workload information between radiologists at different institutions.

As shown, the example exam distributor also includes an allocation manager 212. The allocation manager 212 automatically allocates an exam to a radiologist for review. For example, the allocation manager 212 automatically allocates the exam to the radiologist based on one or more rules defined by the rules creator 210. In some examples, the allocation manager 212 automatically allocates an exam to a preferred radiologist based on the radiologist's current workload or workload threshold, specialty, and/or availability. In other examples, the allocation manager 212 automatically allocates the exam to a radiologist based on exam attributes, such as an exam priority level or a service level agreement requiring the exam to be reviewed within a certain amount of time. In further examples, the allocation manager 212 allocates the exam to a radiologist based on one or more combinations of the aforementioned exam and/or radiologist properties.

The example exam distributor 102 also includes an assignment manager 214. The assignment manager 214 assigns an exam to a radiologist. As described above, the allocation manager 212 automatically allocates the exam to the radiologist. However, prior to the allocated exam being reviewed by the radiologist, the radiologist and/or an administrator can review the allocation of the exam to the radiologist via the display 200 (e.g., by interacting with the examiner user interface 204*a-n* or the administrator user interface 202). Based on, for example, the radiologist's workload, availability, or an exam attribute, the radiologist and/or the administrator can selectively confirm and/or reject the allocation of the exam to the radiologist or decide to redirect the exam to another radiologist for review. The assignment manager 214 facilitates the radiologist's and/or the administrator's decision by confirming assignment and/or acceptance of the exam to the radiologist's workflow.

In other examples, the assignment manager 214 assigns the exam to the radiologist without the allocation manager 212 first allocating the exam to the radiologist. For example, a radiologist, via the user interface 204*a-n* can direct the assignment manager 214 to assign an unallocated exam to the radiologist's work queue. In other examples, one or more rules defined by the rules creator 210 bypass the allocation of the exam to the radiologist and cause the assignment manager 214 to automatically assign the exam to the radiologist's workflow without requiring further confirmation. In other examples, the assignment manager 214 automatically assigns the exam to the radiologist based on radiologist schedules and/or requests for specific radiologists from referring physicians.

In further examples, the assignment manager 214 automatically assigns the exam to the radiologist for substantially immediate review by the radiologist without assigning the exam to the radiologist's work queue. For example, the radiologist can select, via the examiner interfaces 204*a*, to be auto-served exams by the assignment manager 214. In such examples, the assignment manager 214 assigns the exam to the radiologist by delivering the exam to a review and reporting screen via the examiner interface 204*a*. The radiologist reviews the exam and can select to receive another exam for immediate review. In such examples, because the radiologist is reviewing and reporting on the exams in real-time upon exam distribution, the exams are not added to the radiologist's work queue. However, in some examples, statistics such as review efficiency and workload are adjusted to account for exams reviewed in auto-serve mode. Assignment in the auto-serve mode can be based on the load-balancing rules and/or some other pre-defined rules defining priority for exams requiring review.

The example exam distributor 102 also includes a database 216. The database 216 stores information concerning distribution rules, exam allocation information, and/or allocation information. The database 216 also stores information related to one or more radiologists, such as availability and/or profiles. In some examples, the database 216 stores information associated with one or more affiliated institutions in view of exams performed at the individual institutions. The database 216 also stores information provided to the exam distributor 102 via the user input module 206.

In the example shown, the components of the exam distributor 102, including the display module 200, the user input module 206, the profile creator 208, the rules creator 210, the allocation manager 212, the assignment manager 214, and/or the database 218, are in communication with each other via a communications link 218. The communications link 218 may be any type of wired connection (e.g., a databus, a USB connection, etc.) and/or any type of wireless communication (e.g., radio frequency, infrared, etc.) using any past, present, or future communication protocol (e.g., Bluetooth, USB 2.0, USB 3.0, etc.). Also, the components of the example exam distributor 102 can be integrated in one device or distributed over two or more devices.

While an example manner of implementing the exam distributor 102 of FIG. 1 is illustrated in FIG. 2, one or more of the elements, processes and/or devices illustrated in FIG. 2 can be combined, divided, re-arranged, omitted, eliminated and/or implemented in any other way. Further, the display module 200, the user input module 206, the profile creator 208, the rules creator 210, the allocation manager 212, the assignment manager 214, the database 216 and/or, more generally, the example exam distributor 102 of FIG. 2 can be implemented by hardware, software, firmware and/or any combination of hardware, software and/or firmware. Thus, for example, any of the example display module 200, the user input module 206, the profile creator 208, the rules creator 210, the allocation manager 212, the assignment manager 214, the database 216 and/or, more generally, the example exam distributor 102 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example display module 200, the user input module 206, the profile creator 208, the rules creator 210, the allocation manager 212, the assignment manager 214, the database 216, and/or the exam distributor 102 is/are hereby expressly defined to include a tangible computer readable storage device or storage disk such as a memory, a digital versatile disk (DVD), a compact disk (CD), a Blu-ray disk, etc. storing the software and/or firmware. Further still, the example exam distributor 102 of FIG. 2 can include one or more elements, processes and/or devices in addition to, or instead of, those illustrated in FIGS. 8 and 9, and/or can include more than one of any or all of the illustrated elements, processes and devices.

Figure 3:
FIG. 3 illustrates a first example screen of an example graphical user interface associated with the example medical exam distributor of FIG. 1.

FIG. 3 shows an example user interface 126 for interacting with the example exam distributor 102 of FIG. 2. The example user interface 126 includes, for example, the administrator user interface 202 and/or the examiner user interfaces 204a-n of FIG. 2. The example user interface 126 includes one or more screens for interacting with the example exam distributor 102, as will be discussed herein in connection with FIG. 3 and FIGS. 4, 5, and 6 (below).

FIG. 3 depicts an example first screen 300 of the example user interface 126. The example first screen 300 displays information in association with distribution of exams via the exam distributor 102. In some examples, the first screen 300 is a dashboard providing an overview of one or more exams requiring review across a radiology department, a hospital, and/or a network of departments and/or healthcare institutions.

The first screen 300 includes an exam identifier 302. In some examples, the exam identifier 302 is a visual representation of one or more exams requiring review by a radiologist. The exam identifier 302 includes, for example, a name of a patient on which the exam was conducted, an image of the patient, a procedural code, a body part on which the exam was conducted, an exam modality, and/or a time at which the exam was conducted. The exam identifier 302 can also include other, customizable information regarding the exam.

Exam attribute identifiers 304, 306, 308 that are representative of one or more exam attributes can also be displayed on the first screen 300. For example, an exam priority indicator 304 may represent a priority level associated with an exam. If a patient is in critical condition and the exam requires urgent review by a practitioner, the exam priority indicator 304 is highlighted. Other exam attribute identifiers 306, 308 indicate whether an exam has been dictated by a practitioner, a name of an prescribing radiologist, a name of radiologist to which the patient has been referred, whether the exam is associated with a service level agreement that specifies a time period for review of the exam in order to receive payment and/or a payment schedule, and/or a relative value unit representative of a difficulty level of the exam. In some examples, the exam attribute identifiers 306, 308 include an alert displayed on the example first screen 300 to indicate that an exam is reaching a time limit for review. Other exam attributes can be selectively displayed, hidden, and/or removed from the example first screen 300. Also, in some examples, the exam attribute identifiers 306, 308 are shared across the administrator and examiner user interfaces 202, 204a-n to provide for monitoring of exam urgency levels across the network and to facilitate a response, if necessary, by the administrator and/or radiologists with respect to prioritizing review of the exams.

The example first screen 300 of the user interface 126 displays one or more exam status identifiers 310, 312, 314. The exam status identifiers 310, 312, 314 are visual indications of the status of the distribution of an exam to a radiologist based on implementation of the exam distributor 102 (including, for example, implementation of the rules defined by the rules creator 210 of FIG. 2). Further, the exam status identifiers 310, 312, 314 dynamically update in response to communicative interactions with the exam distributor 102 via, for example, the user interface 126.

Figure 4:
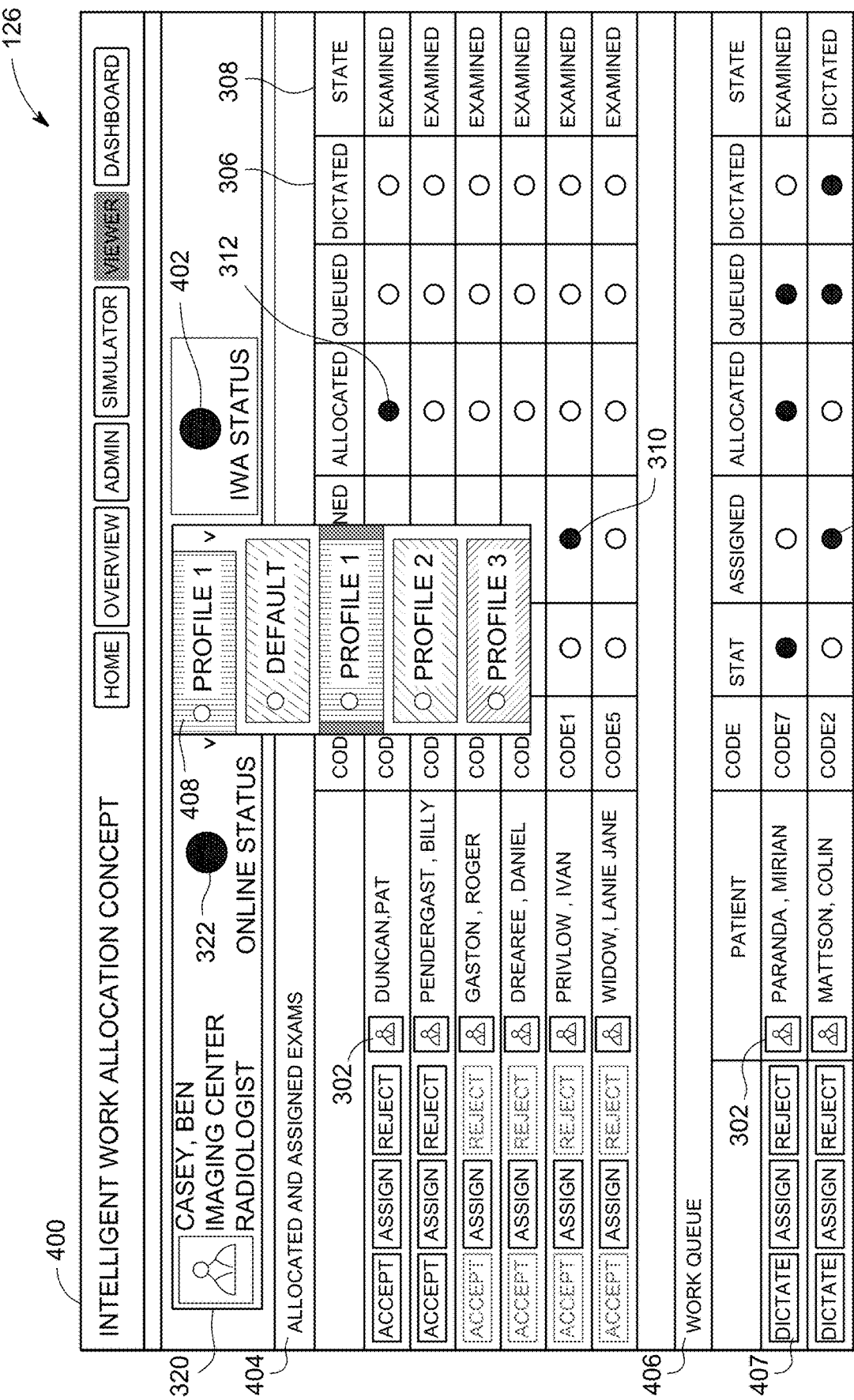
FIG. 4 illustrates a second example screen of an example graphical user interface associated with the example medical exam distributor of FIG. 1.

For example, a first exam status identifier 310 indicates whether an exam has been assigned, via, for example, the assignment manager 214, to a radiologist. A second exam status identifier 312 indicates whether the exam has been allocated to a radiologist, via, for example, the allocation manager 212. A third exam status identifier 314 represents whether, for example, an exam assigned to a radiologist has been accepted for review by the radiologist and moved to the radiologist's work queue (FIG. 4).

The example first screen 300 selectively displays an examiner scorecard 316. In some examples, the scorecard 316 is displayed on a different screen of the user interface 126. The scorecard 316 includes an examiner summary viewer 318. As shown in FIG. 3, the examiner summary viewer 318 includes a table containing information about one or more radiologists, including, for example, name, specialty, experience level, seniority, and/or total number of assigned, allocated, and/or accepted exams. In some examples, the example first screen 300 provides a messaging and/or other communication tool for users to interact with radiologists listed in the scorecard 316.

A user interacting with the first screen 300 can select to view additional information about a radiologist listed in the examiner summary viewer 318. Upon selecting a radiologist, the screen 300 of the user interface 126 displays, for example, an examiner identifier 320. The examiner identifier 320 includes, for example, an image of the selected radiologist. An examiner availability indicator 322 can also be displayed. The examiner availability indicator 322 is a visual representation of an online status of a radiologist. For example, if a radiologist is accessing, for example, the radiology information system 106 of FIG. 1, the radiologist can be considered to be available for purposes of reviewing the allocated exam. The examiner availability indicator 322 represents a local presence of the radiologist, a remote presence, an offline status, and/or another status associated with an availability of the radiologist. In some examples, the radiologist can selectively set the status of the examiner availability indicator 322, for example, via the first screen 300 or another screen (e.g., an example second screen 400 of FIG. 4 below). In further examples, the examiner availability indicator 322 is associated with one or more profiles created by the radiologist. For example, the radiologist can select a profile as an active profile (FIG. 4), which may result in the examiner availability indicator 322 reflecting the availability of the radiologist based on the selected profile.

Any of the exam identifier 302; the exam priority indicator 304; exam attribute identifiers 306, 308; exam status identifiers 310, 312, 314; the scorecard 316; the examiner summary viewer 318; the examiner identifier 320; and/or the examiner availability indicator 322 can be dynamically updated based on, for example, implementation of the exam distributor 102 and/or a user's interaction with the user interface 126, including, for example, the administrator interface 202 or the examiner user interfaces 204a-n. In some examples, the identifiers, indicators, and/or scorecard of the example first screen 300 are updated to reflect that a radiologist is reviewing exams in auto-serve mode. Further, any of the exam or examiner identifiers and/or indicators can be represented on the first screen 300, or any other screens of the user interface 126, by a variety of means of visual display, including, but not limited to, being flagged/unflagged, highlighted/unhighlighted, displayed/hidden, and/or activated/deactivated. The identifiers and indicators displayed on the example first screen 300 can also be selectively tailored based on, for example, whether the example first screen displays information for a radiology department at a hospital or across a network of healthcare institutions. Also, the identifiers and indicators of the example first screen 300 can be selectively represented by more or fewer icons. For example, instead of multiple exam status identifiers 310, 312, 314 to indicate the distribution status of an exam, a single exam status identifier can be provided. In some examples, the single exam status identifier can be selectively expanded or collapsed to provide more details about the exam distribution status.

In operation, for example, the example first screen 300 of the user interface 126 provides a user, such as one or more radiologists in a network, with an overview of one or more exams requiring review and associated exam attribute information. The first screen 300 further portrays information concerning distribution of one or more exams to a reviewing radiologist. Additionally, the first screen 300 allows a user to selectively view a summary of one or more radiologists' workloads and/or availability status. In some examples, the first screen 300 provides a snapshot of exam distribution status as well as the factors, such as radiologist availability, that influence workflow distribution of exams by the exam distributor 102. Further, in some examples, a user considers the information provided on the first screen 300 in managing distribution of exams. Thus, the example first screen 300 serves as a dashboard for an overview of the exam distribution system and/or a launch pad for further review of workload allocation.

FIG. 4 illustrates an example second screen 400 of the example user interface 126 for interacting with the exam distributor 102 of FIG. 2. The second example screen 400 displays, for example, information concerning a radiologist's workload based on exams assigned and/or allocated to the radiologist by the exam distributor 102. In some examples, the second screen 400 serves as a workflow notification page for a radiologist by listing exams that the radiologist has been assigned to review, for example, on a certain day or in a certain order. In further examples, the second screen 400 provides for a radiologist to designate a capacity in which the radiologist is available to review exams, which may determine the allocation of exams to the examiner by the exam distributor 102 and, as such, the exams that are identified on the example second screen 400.

In some examples, a user views the second example screen 400 by selecting an examiner identifier 320 associated with a particular radiologist from the examiner summary viewer 318 of the example first screen 300 (FIG. 3). In other examples, a user reaches the example second screen 400 via links provided on one or more other screens of the example user interface 126, or directly upon accessing the user interface 126.

A first portion of the screen 400 displays identifying information about the radiologist, including, for example, the examiner identifier 320 and/or the examiner availability indicator 322. In some examples, a radiologist sets the status of the examiner availability indicator 322 by interacting with the example screen 400. The status of the examiner availability indicator 322 (e.g., available, remote, away, offline) can be selected via, for example, a drop-down menu or another means of changing the status displayed by the examiner availability indicator 322.

The screen 400 also includes a workload availability identifier 402. The workload availability identifier 402 indicates a radiologist's availability to be allocated and/or assigned exams. For example, based on one or more load-balancing rules defined by the rules creator 210, the allocation manager 212 and/or the assignment manager 214 (FIG. 2) can refrain from allocating and/or assigning exams to the radiologist if the radiologist's workload has surpassed a threshold. Accordingly, the workload availability indicator 402 can be deactivated to visually represent that the radiologist is not to be allocated and/or assigned exams. In other examples, the workload availability indicator 402 is activated to reflect that the examiner is available to receive exams based on a current state of the radiologist's workload. In some examples, the status of the examiner availability indicator 322 is distinct from the workload availability indicator 402. For example, a radiologist can access and/or log into the radiology information system 106 (FIG. 1) and thus, have an online presence, but is unable to be allocated and/or assigned exams because of a workload threshold.

A second portion of the example second screen 400 displays an allocated/assigned exam summary 404. The allocated/assigned exam summary 404 includes a listing of one or more exams that have been allocated to the radiologist by the allocation manager 212 (FIG. 2) and/or assigned to the radiologist by the assignment manager 214 (FIG. 2). In some examples, one or more allocated and/or assigned exams are represented in the allocated/assigned exam summary 404 by the exam identifier 302 and/or the exam attribute identifiers 304, 306, 308. In further examples, the allocated/assigned exam summary 404 displays one or more of the exam status identifiers 310, 312, 314 associated the exam. The exams in the allocated/assigned exam summary 404 can be attributed to assignment by an administrator and/or a radiologist. The exams can also appear in the allocated/assigned exam summary 404 as a result of assignment based on the radiologist's schedule and/or because the radiologist was requested by a referring physician.

A third portion of the example second screen 400 of the user interface 126 displays an examiner work queue 406. The examiner work queue 406 contains exams that have, for example, been accepted by the examiner for review, as will be described below in connection with FIG. 6. Additionally or alternatively, the examiner work queue 406 contains exams that a radiologist has assigned to him/herself to review prior to distribution of the exam to the radiologist by the allocation manager 212 and/or the assignment manager 214. For example, a radiologist can view a status of one or more exams via the example first screen 300 using, for example, the examiner user interface 204a. The radiologist can decide to assign one or more the exams to him/herself without the exam being distributed to the radiologist by the allocation manager 212 and/or the assignment manager 214. In other examples, if a radiologist is no longer available to receive exams after reaching a workload threshold, as represented by the workload availability indicator 402, one or more exams can be populated in the examiner work queue 406, but the allocation/assignment summary 404 is empty.

An exam can be represented in the examiner work queue 406 by, for example, the exam identifier 302, the exam attribute identifiers 304, 306, 308, and/or one or more of the exam status identifiers 310, 312, 314 associated with the exam. In some examples, the third exam status identifier 314 is flagged to reflect that the exam is in the radiologist's examiner work queue 406.

When an exam is in a radiologist's examiner work queue 406, the radiologist has confirmed that he/she will be reviewing the exam and/or is required to review the exam based on a decision by an administrator. The radiologist can review the exam while accessing the radiology information system 106 via, for example, the workstation 114 (FIG. 1). For example, the radiologist can access the exam via the examiner work queue 406 such that selecting, for example, the exam identifier 302 opens the exam in an exam review and reporting screen of the examiner interface 204a-n. Additionally or alternatively, in some examples, the exam is not added to the examiner's work queue 406, but rather, the radiologist reviews the exam in real-time upon allocation of the exam via the exam review and reporting screen of the examiner interface 204a-n. In such examples, although the exam does not appear in the examiner's work queue 406, the radiologist's exam-reviewing activity is recorded by the exam distributor 102.

In some examples, the radiologist may decide to review an exam in the examiner work queue 406 while working remotely, for example, from a location where the radiologist is not accessing the radiology information system 106 and/or the user interface 126. In such examples, the example second screen 400 provides for the radiologist to selectively update the examiner availability indicator 322 to reflect that the radiologist is offline, but working.

Further, the example second screen 400 provides for the radiologist to indicate that the radiologist is working on the exam remotely. For example, the examiner work queue 406 of the example second screen 400 includes an exam decision tool 407 that allows the radiologist to take selective action with respect to exams identified in the radiologist's examiner work queue 406. As will be described below in connection with FIG. 6, the exam decision tool 407 facilitates acceptance and/or rejection of an exam from the examiner's work queue 406. In other examples, the exam decision tool 407 provides for the radiologist to optionally indicate that he/she will be reviewing the exam offline. The exam decision tool 407 includes a flag, button, menu selection, and/or other means for the radiologist to indicate via the second screen 400 that the exam is being reviewed offline. Such information regarding the status of the exam is considered by the exam distributor 102 in distributing other exams to the radiologist and/or monitoring the status of the assigned exam and/or the examiner's work queue 406. In such a manner, the example second screen 400 allows a radiologist to manage his/her workflow with respect to working online and/or offline.

After working remotely, the radiologist can re-access the radiology information system 106, the user interface 126 and/or the example second screen 400. The radiologist can update the examiner availability indicator 322 to reflect that the radiologist is online and/or available. The exam distributor 102 provides for the radiologist, for example, to upload information related to the exam that was reviewed while the radiologist was offline. Such information is stored in the database 216. For example, the exam status identifiers 310, 312, 314; the exam attribute identifiers 306, 308; and/or other identifiers and indicators provided on the example first and second screens 300, 400 can be dynamically updated in response to the radiologist accessing the user interface 126 after reviewing an exam while offline. The exam distributor 102 updates and/or synchronizes information about the exam reviewed offline upon the radiologist re-accessing the user interface 126. In such a manner, the exam distributor 102 dynamically monitors the status of the exam and provides current exam information to other radiologists and/or administrators in the network.

Figure 5:
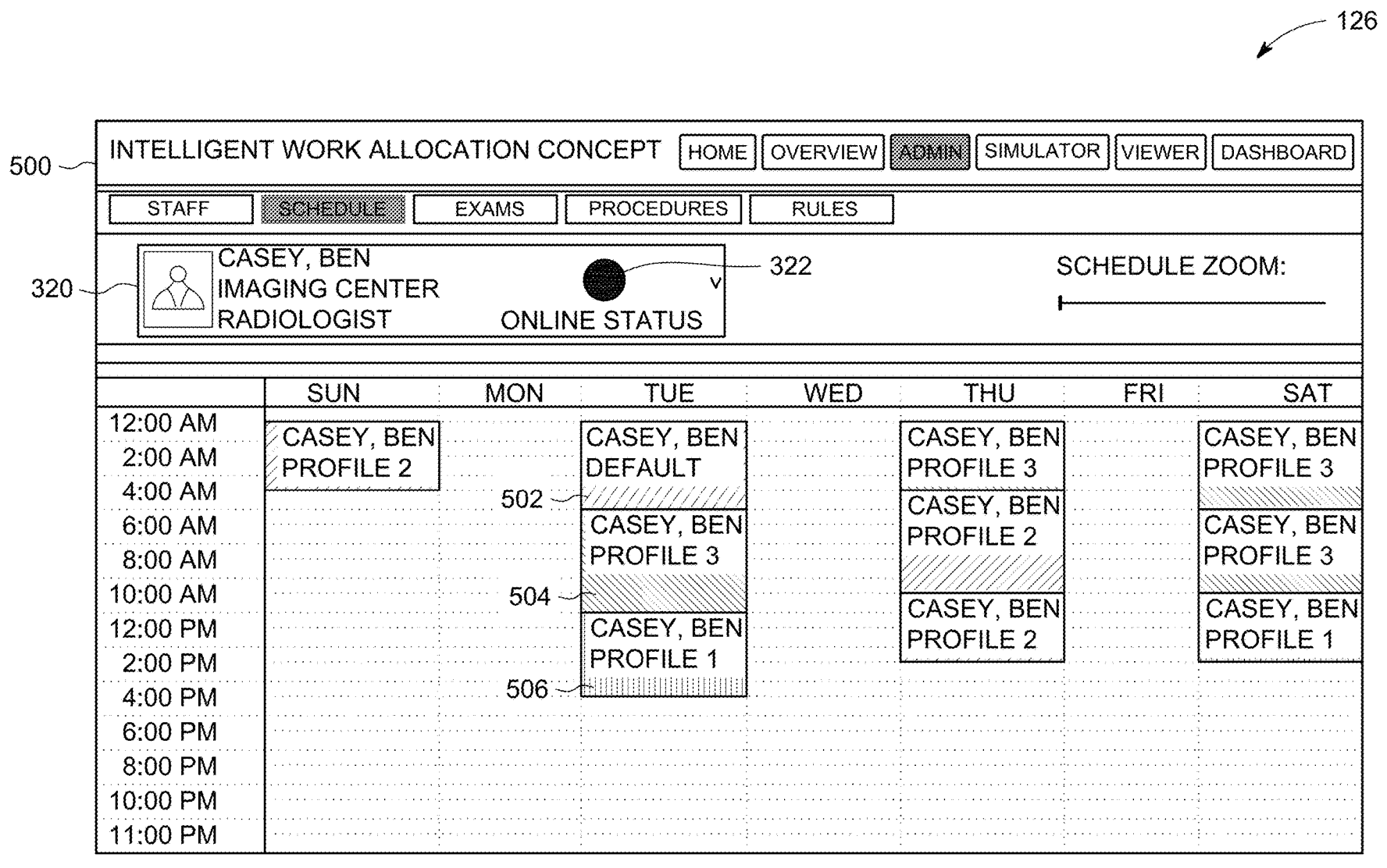

The second screen 400 also includes a profile selector 408. As described above, the profile creator 208 (FIG. 2) optionally provides for a radiologist to create one or more profiles. The one or more profiles can be based on, for example, availability and/or specialty practiced during certain times or on particular days of the week (FIG. 5, below).

A profile affects the distribution of exams to the radiologist by the allocation manager 212 and/or the assignment manager 214. For example, when a radiologist is associated with a certain profile, he/she may be allocated and/or assigned no exams, only a certain number of exams, and/or only exams having certain exam attributes.

The profile selector 408 provides for a radiologist to designate a profile as an active profile. By selecting a profile on the example second screen 400 (e.g., via a drop down menu), the radiologist can designate the capacity in which he/she is currently able to receive exams. Selecting a profile as an active profile updates, for example, the examiner availability identifier 322 and/or the workload availability identifier 402 based on the parameters of the selected profile. The display status of the examiner availability identifier 322 and/or the workload availability identifier 402 is updated on the user interfaces 202, 204a-n accessed by, for example, the other radiologists in the network, to provide an indication of the current availability of the radiologist to review exams. Additionally or alternatively, the exam distributor 102 dynamically applies the parameters of the active profile when allocating exams to the radiologist as well as to other radiologists in the network. In some examples, the exam distributor 102 distributes exams to the radiologist based on the scheduling attributes associated with the selected profile.

The profile selector 408 also provides for a user, such as the radiologist, to view the allocation/assignment summary 404 and/or the examiner work queue 406 for a selected profile. For example, upon selecting a profile via the profile selector 408, the second screen 400 dynamically updates to display only exams in the examiner work queue 406 that the radiologist is assigned to review when the radiologist is associated with the selected profile. From the example second screen 400, the radiologist can use the profile selector 408 to view exams distributed on a profile-specific basis.

In operation, the example second screen 400 of the user interface 126 provides for a user to view a radiologist-specific workload. The example second screen 400 can be viewed by a radiologist to provide the radiologist with a listing of exams that have been allocated to, assigned to, and/or accepted by the radiologist. Additionally or alternatively, the example second screen 400 enables the radiologist to designate his/her availability to review exams, by, for example, updating an online status indicator and/or selecting a profile as an active profile to influence allocation of the exams by the exam distributor 102. In further examples, the example second screen 400 is viewed by one or more radiologists in a shared network to view the allocation and/or assignment of exams within the network. In viewing, for example, the availability of a particular radiologist and/or exams assigned to the radiologist, the example second screen 400 promotes collaboration and/or consultation among radiologists reviewing exams. Thus, the example second screen 400 provides for a radiologist-level review of exam distribution and workload allocation and serves as tool for facilitating shared interactions among reviewing radiologists.

Also, the example second screen 400 provides for the radiologist to indicate that he/she is reviewing an exam offline by updating one or more status identifiers associated with the exam and/or radiologist's availability. Further, when the radiologist updates his/her availability after being offline, the exam distributor 102 provides for information about the exam reviewed offline to be dynamically updated so that the current status of the exam is accurately reflected across the user interfaces accessed by the radiologists and/or administrators of the network.

FIG. 5 illustrates an example third screen 500 of the example user interface 126 for interacting with the exam distributor 102 of FIG. 2. The example third screen 500 provides for a user, such as a radiologist, to optionally create and/or view profiles that are used in managing distribution of exams to the radiologist in connection. The creation and/or modification of profiles via the example third screen 500 can be implemented association with the profile creator 208 (FIG. 2). For example, as shown in FIG. 5, the radiologist can selectively affiliate certain times and/or days with a profile by designating portions of the day to be associated with one or more profiles. For example, a first profile 502, a second profile 504, and/or a third profile 506 represent one or more parameters, including, but not limited to, the radiologist's availability, specialty, expertise, location, preferred exam attributes at different times of the day. In some examples, one or more of the example profiles 502, 504, 506 is a default profile, representing, for example, a default availability and/or specialty of the radiologist. As described above, in allocating and/or assigning exams to the radiologist and/or other radiologists in the network, the exam distributor 102 incorporates the characteristics, parameters, and/or criteria associated with one or profiles when implementing the load-balancing rules defined by the rules creator 210.

The example third screen 500 displays, for example, the examiner identifier 320 and/or the examiner availability indicator 322. In some examples, the radiologist selects and/or updates the status of the examiner availability indicator 322 from the third screen 500. The example third screen 500 can be accessed from the example second screen 400, via, for example, the profile selector 408 and/or other links provided on the example second screen 400 and/or other screens of the user interface 126. Also, upon creating a profile via the example third screen 500, the profile appears in the profile selector 408 of the example second screen 400. In such as manner, the user interface 126 allows for a user to optionally create one or more profiles and select a profile as an active profile for managing workflow and exam distribution.

Figure 6:
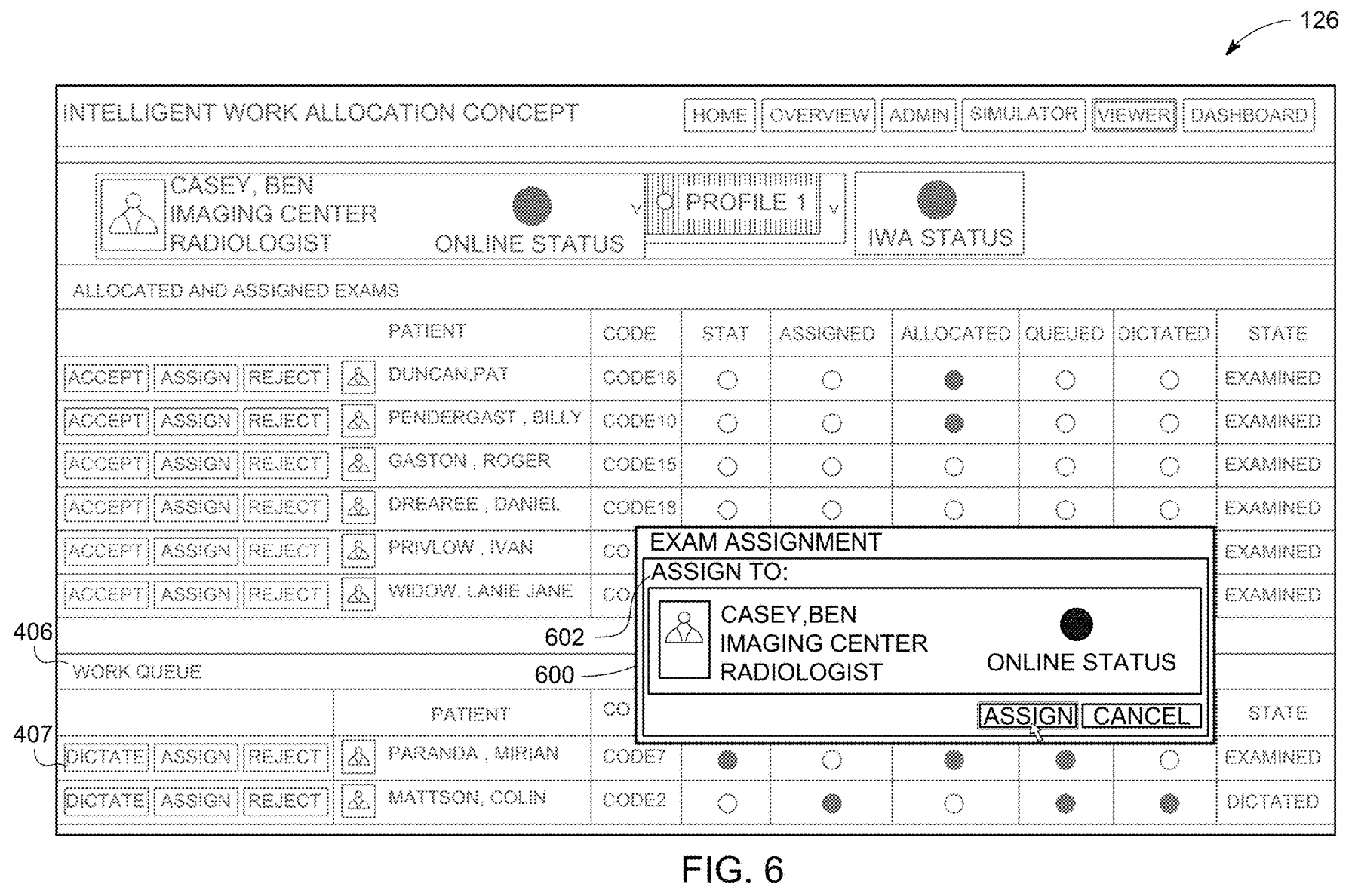

FIG. 6 illustrates an example fourth screen of the example user interface 126 for interacting with the exam distributor 102 of FIG. 2. As shown in FIG. 6, the example fourth screen 600 can be accessed from the example second screen 400. The exam decision tool 407 associated with the examiner work queue 406 provides menu options to facilitate acceptance, rejection, and/or reassignment of the exam, which can be further implemented via the example fourth screen 600. In other examples, the example fourth screen 600 is accessed from the example first screen 300, by for example, selecting an exam identifier 302 displayed on the first screen 300.

The example fourth screen 600 includes an exam assignment tool 602. The exam assignment tool 602 can be accessed via the first screen 300 (FIG. 3), the second screen 400 (FIG. 4), and/or any other screens of the administrator user interface 202. For example, in FIG. 6, the exam assignment tool 602 is accessed via the example second screen 400.

In some examples, the exam assignment tool 602 facilitates acceptance and/or rejection of an exam allocated to a radiologist. For example, the radiologist can interact with the exam assignment tool 602 to accept an exam that has been allocated to the radiologist by the allocation manager 212. The radiologist can select a menu option provided by the exam decision tool 407 associated with the allocated exam via the example second screen 400, which causes the exam assignment tool 602 to display to facilitate assignment and/or acceptance of the allocated exam. Upon acceptance of the exam via the assignment tool 602, one or more of the allocation/assignment summary 404, the examiner work queue 406, and/or the exam status identifiers 310, 312, 314 dynamically updates to reflect the status of the exam for display on the administrator user interface 202 and/or the examiner user interfaces 204a-n. For example, the display of the exam identifier 302 associated with the accepted exam moves from the allocation/assignment summary 404 to the examiner work queue 406 to reflect that the radiologist has accepted the exam. In some examples, upon acceptance of the allocated exam by the radiologist, the exam is no longer available for allocation by the allocation manager 212.

In other examples, if the radiologist declines to review the assigned exam, the exam identifier 302 is be no longer be displayed in the allocation/assignment summary 404 and/or the examiner work queue 406 for the radiologist. In some examples, the assignment tool 602 provides for the radiologist and/or an administrator to reassign the exam to another radiologist. Upon rejection and/or reassignment, the exam distributor 102 automatically allocates another exam to the radiologist. In some examples, the exam distributor 102 stores information regarding acceptance and/or rejection of allocated exams by the radiologist as part of the load-balancing rules of the rules creator 210.

In further examples, the radiologist can use the exam assignment tool 602 to assign and/or accept an exam that has not been allocated to a radiologist. For example, the radiologist can view an exam identifier 302 displayed on the first screen 300 (FIG. 3) representing an exam that has not been allocated to a radiologist. The radiologist can decide to assign the unallocated exam to him/herself. In such examples, the exam assignment tool 602 can be accessed via the first screen 300 by selecting the exam identifier 302 to facilitate manual assignment of the unallocated to the radiologist. Also, in such examples, one or more of the allocation/assignment summary 404, the examiner work queue 406 and/or the exam status identifiers 310, 312, 314 displayed on the screens of the user interface 126, including the administrator interface 202 and/or the examiner user interfaces 202a-n update to reflect the status of the exam.

In some examples, the exam assignment tool 602 is accessed by an administrator via the administrator user interface 202. For example, in some examples, an administrator plays a role in assigning exams to a radiologist and the radiologist may or may not have the option to accept and/or decline assigned exams. For example, an administrator viewing the fourth screen 600 via the administrator user interface 202 can decide to assign an exam that has been allocated to a radiologist to the radiologist, based on, for example, the radiologist's workload as displayed via the example second screen 400 and/or the metrics provided in the scorecard 316 (FIG. 3). In some examples, the administrator selects an exam identifier 302 associated with the allocated exam via the example second screen 400, which causes the exam assignment tool 602 to display to facilitate assignment of the allocated exam. Using the exam assignment tool 602, the administrator assigns the allocated exam to the radiologist. Upon assignment of the exam to the radiologist, the exam identifier 302 appears in the allocated/assignment summary 404 associated with the radiologist. Additionally or alternatively, in some examples, the patient identifier appears in the examiner's work queue 406 associated with the radiologist. In other examples, an administrator defines one or more rules via the rules creator 210 for automatic assignment of an exam to the examiner work queue 406 of the radiologist.

In further examples, if the radiologist has declined to review the assigned exam, the administrator can override the rejection of the exam via the exam assignment tool 602 and/or by defining one or more automatic rules via the rules creator 208. In other examples, the administrator and/or the exam distributor 102 can manually and/or automatically override the radiologist's availability, profile settings, preferred exam attributes, and/or one or more rules defined by the rules creator 208 using the exam assignment tool 602 to facilitate assignment of the exam to the radiologist. For example, the administrator can assign an exam to a radiologist whose availability indicator indicates that he/she is offline.

In other examples, the radiologist does not have an option to accept or decline an assigned exam via the exam assignment tool 602. In such examples, only the administrator has access to the exam assignment tool 602. In those examples, upon assignment of the exam to the radiologist, the exam identifier 302 is displayed in the examiner work queue 406 and can be viewed, but not removed, from the examiner work queue 406 by the assigned radiologist via the examiner user interface 204*a*.

In operation, the example fourth screen 600 provides for the acceptance of an allocated exam by a radiologist and facilitates inclusion of the allocated exam in the radiologist's work queue. The example fourth screen 600 also provides for a radiologist to reject and/or reassign an allocated exam and/or manually assign an unallocated exam to the radiologist's workflow. In further examples, an administrator defines a degree to which the radiologist is capable of accepting, rejecting, and/or reassigning an allocated exam through manual review and/or by defining automatic rules related to assignment of exams.

Figure 7:
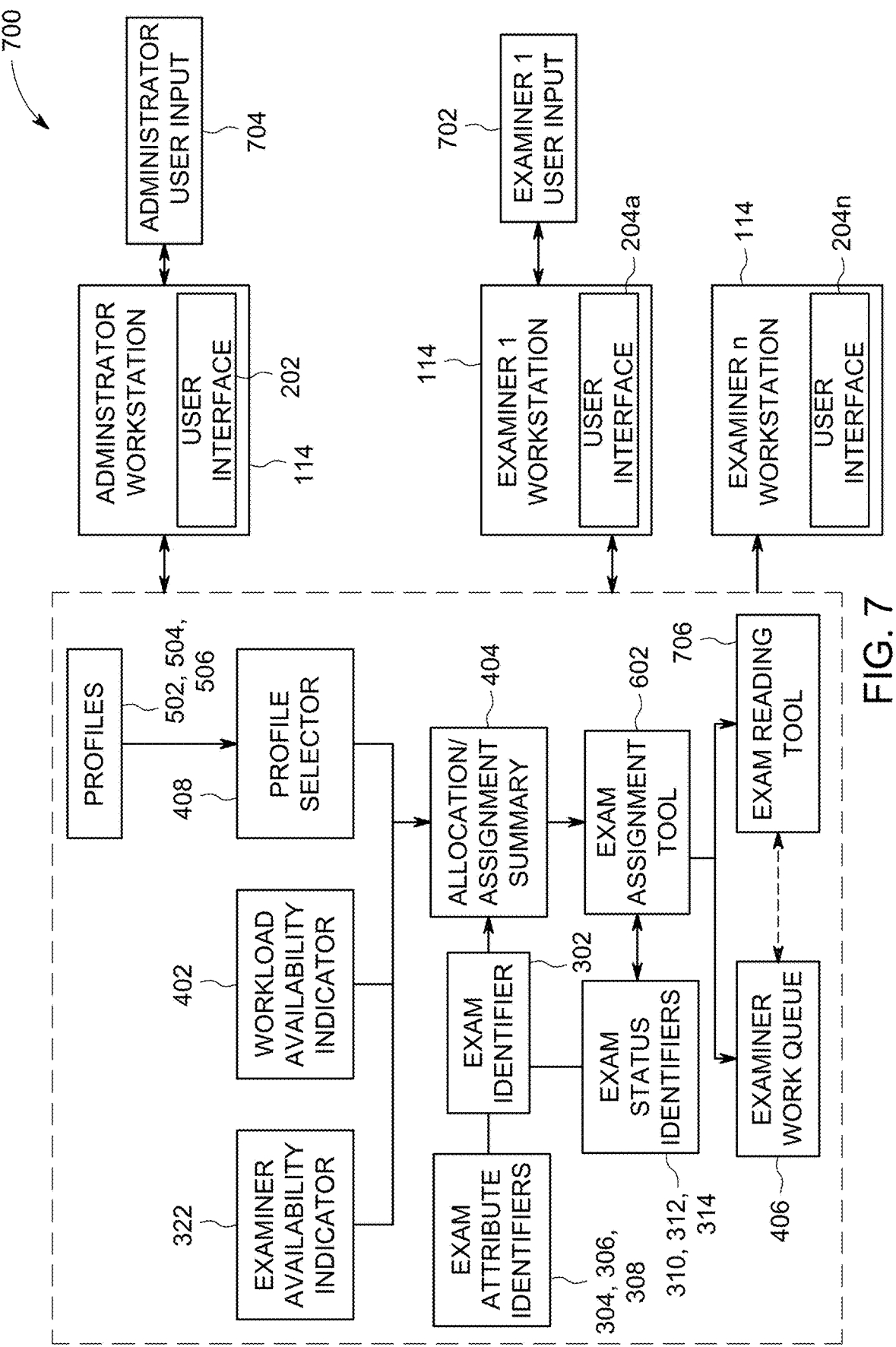
FIG. 7 depicts an interactive relationship between the first, second, third, and fourth example screens of FIGS. 3-6.

FIG. 7 depicts an interactive relationship 700 between the components of the screens 300, 400, 500 of the user interfaces 126, 202, 204*a-n* and users via one or more administrator and/or examiner workstations 114. For example, a first radiologist can access the examiner user interface 204*a* at a workstation 114 and provide one or more examiner user inputs 702 via the examiner user interface 204*a*. Additionally or alternatively, an administrator can access the administrator user interface 202 at the respective workstation 114 and provide one or more administrator user inputs 704 via the administrator user interface 202. Also, one or more radiologists n in a shared network can view, for example, the examiner availability indicator 322 and/or the examiner work queue 406 associated with the first radiologist via the examiner user interface 204*n* accessed at the respective workstation 114.

As shown in FIG. 7, the first radiologist views one or more of the components of the example first, second, and/or third screens 300, 400, 500, 600 via the user interface 204*a*. As described above, the example screens 300, 400, 500, 600 display components related to exam distribution. For example, the exam identifier 302 is displayed along with exam attribute identifiers 304, 306, 308 as well as the exam status indicators 310, 312, 314. Additionally or alternatively, the first radiologist can view one or more of the examiner availability indicator 322, the workload availability indicator 402, the profile selector 408, and/or, more generally, the allocation/assignment summary 404 via the example first, second, third, and/or fourth screens 300, 400, 500, 600.

The first radiologist can provide one or more user inputs 702 via the examiner user interface 204*a*. For example, the first radiologist can update the examiner availability indicator 322 via the screens 300, 400, 500 to reflect that the first radiologist is online, remotely working, and/or not available.

The first radiologist can also select a profile 502, 504, 506 via the profile selector 408 of the example second screen 400. As described above, one or more components of the screens 300, 400, 500, 600 updates based on a profile selection, including, for example, the examiner availability indicator 322, the workload availability indicator 402, the allocation/assignment summary 404, and/or the examiner work queue 406. Also, as described above, the user input 702 by the first radiologist to accept an allocated exam and/or manually assign an unallocated exam via the exam assignment tool 602 dynamically updates the examiner's work queue 406.

Additionally or alternatively, the first radiologist can provide a user input 702 to open the assigned and/or accepted exam in an exam reading tool 706. In some examples, the exam reading tool 706 is a screen accessible via the examiner user interface 204*a-n* that provides for viewing of the exam (e.g., an x-ray) and reporting on the exam by the first radiologist. In some examples, the first radiologist provides the user input 702 to direct the assigned exam to open in the exam reading tool 706 and bypass the examiner work queue 406. In such examples, the exam reading tool 706 provides for substantially immediate review of the assigned exam by the first radiologist. Also, in some examples, the first radiologist performs successive review of assigned exams via the exam reading tool 706. For example, a first exam is assigned via the exam assignment tool 602 and opened in the exam reading tool 706. After the first radiologist reviews the first exam, the first radiologist provides a user input 702 via the exam reading tool 706 indicating that first radiologist is ready to review another exam. In response to such a user input, a second exam that has been assigned to the first radiologist is directly delivered to the exam reading tool 706 for review. In some examples, the exam status indicators 310, 312, 314 dynamically update to reflect that the exam is being reviewed by the first radiologist in an auto-serve mode.

In other examples, the accepted and/or assigned exam is first placed in the examiner work queue 406, where the exam is represented by the exam identifier 302. The exam is then opened in the exam reading tool 706 at a later time in response to, for example, a user input 702 by the first radiologist (e.g., selecting the exam identifier 302). In further examples, the first radiologist selectively moves between the examiner work queue 406 and the exam reading tool 706 to select an exam from the examiner work queue 406 for review via the exam reading tool 706, return to the examiner work queue 406 after completing the exam review for further workload management, and optionally select another exam for review via the exam reading tool 706. In some examples, the exam status indicators 310, 312, 314 dynamically update to reflect that the exam is in the examiner work queue 406 and/or has been reviewed.

Changes to the one or more components of the screens 300, 400, 500, 600 in response to the user inputs 702 by the first radiologist can impact the allocation and/or assignment of exams by the exam distributor 102 to the first radiologist as well as to one or more radiologists n. As illustrated in FIG. 7, changes to the one or more components of the screens 300, 400, 500, 600 in response to the user inputs 702 by the first radiologist are dynamically shared via the administrator user interface 202 and/or the examiner user interface 202*n* associated with one or more other radiologists in the network. For example, in response to a change in a status of the examiner availability status 322 associated with the first radiologist from "available" to "unavailable", the exam distributor 102 automatically allocates an exam that would have been assigned to the first radiologist to a second radiologist n. In other examples, the second examiner n views the examiner availability indicator 322 indicating that the first radiologist is available via the examiner user interface 204n. In view of the availability of the first radiologist, the second radiologist n decides, for example, to reassign an exam to the first radiologist, facilitate an exchange of allocated exams, and/or send a message to the first radiologist.

In some examples, the administrator provides one or more administrator user inputs 704 related to, for example, assignment of exams, workload thresholds for first radiologists and/or other radiologists in the shared network, exam attributes, and/or other administrative criteria related to exam distribution. The user inputs 704 by the administrator result in dynamic updates to the components of the screens 300, 400, 500, 600 as viewed by the radiologists via the examiner user interfaces 204a-n. For example, upon viewing the allocation/assignment summary 404 associated with the first radiologist, the administrator may decide to assign the exam to the first radiologist. Such an assignment dynamically updates the examiner work queue 406 associated with the first radiologist and viewable via the examiner user interfaces 204a-n. In other examples, the administrator can implement one or more rules modifying a workload threshold of the first radiologist, as represented by the workload availability indicator 402. Such a change in the workload availability indicator 402 of the first radiologist impacts the distribution of exams to other radiologists n in the network by the exam distributor 102. Thus, in such a manner, the exam distributor 102, the user interface 126, and, more generally, the radiology information system 106 provide for a community-oriented exam distribution and workload management system.

Figure 8:
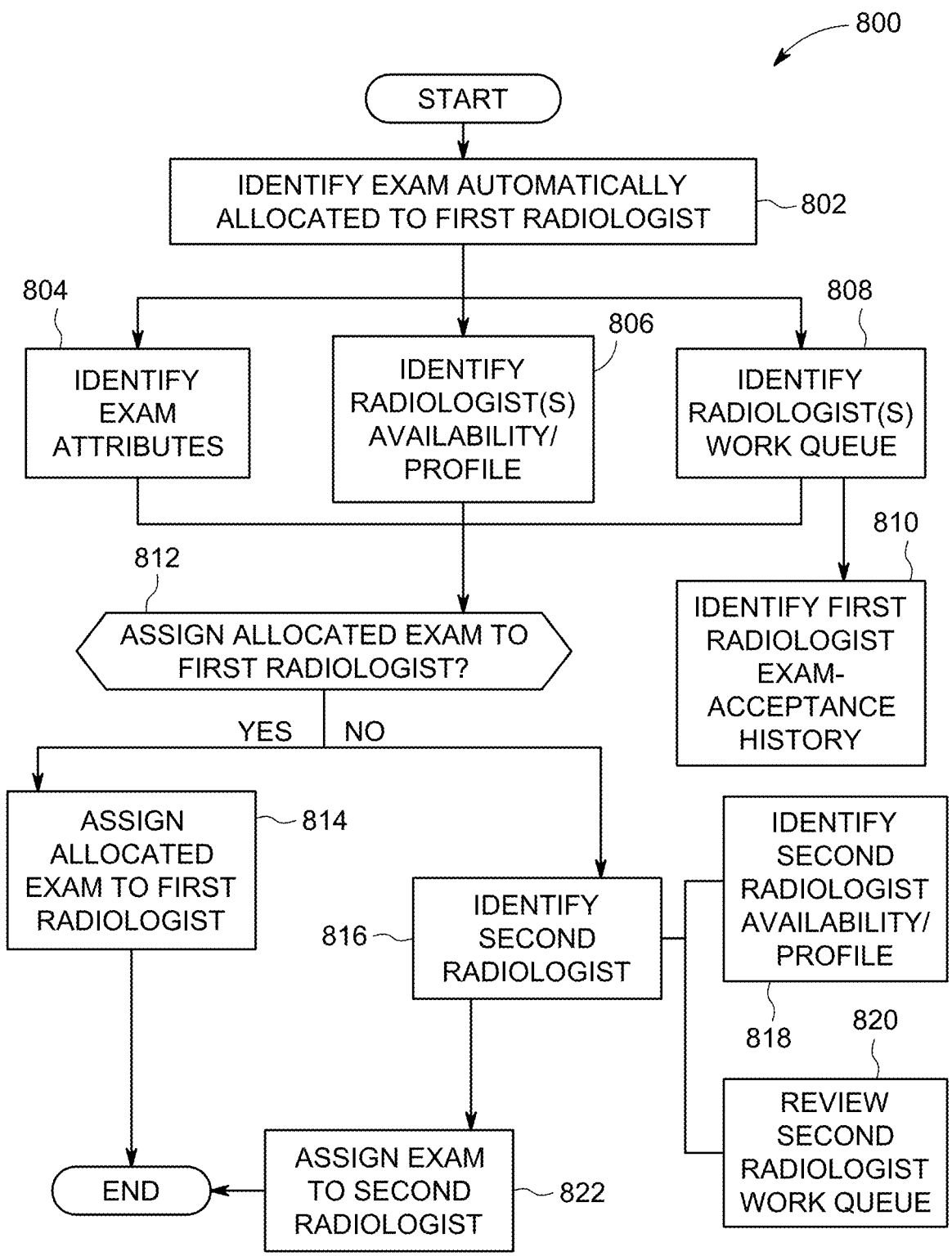
FIG. 8 is a flow diagram illustrating an example method for distributing a medical exam via an example graphical user interface associated with the example medical exam distributor of FIG. 1.
Figure 9:
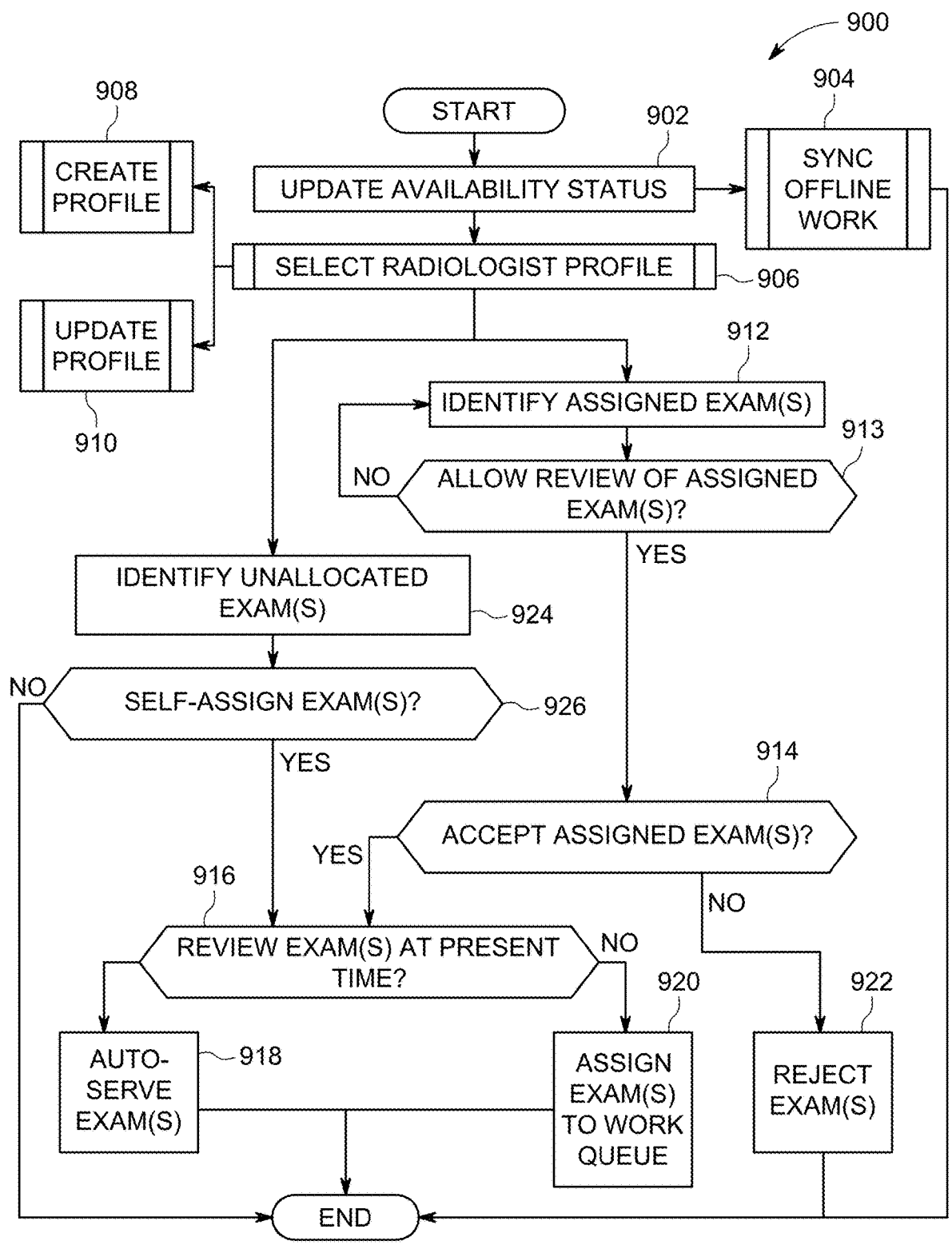
FIG. 9 is a flow diagram illustrating an example method for accepting assignment of a medical exam via an example graphical user interface associated with the example medical exam distributor of FIG. 1.

A flowchart representative of example machine readable instructions for implementing the example exam distributor 102 of FIG. 2 is shown in FIGS. 8 and 9. In these examples, the machine readable instructions comprise a program for execution by a processor such as the processor 1012 shown in the example processor platform 1000 discussed below in connection with FIG. 10. The program can be embodied in software stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowchart illustrated in FIGS. 8 and 9, many other methods of implementing the example exam distributor 102 can alternatively be used. For example, the order of execution of the blocks can be changed, and/or some of the blocks described can be changed, eliminated, or combined.

As mentioned above, the example processes of FIGS. 8 and 9 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 8 and 9 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 8 illustrates a flow diagram of an example method 800 to distribute a medical exam to a radiologist. The example method 800 implements the exam distributor 102 of FIG. 2. In particular, the example method 800 includes a method for assigning a medical exam to a radiologist via the administrator user interface 202 of FIG. 2. In some examples, the example method 800 can be performed manually by an administrator. In other examples, the example method 800 can be implemented via one or more rules defined by, for example, the administrator via the rules creator 210 (FIG. 2).

The example method 800 begins at block 802 with identifying an exam that has been automatically allocated to a first radiologist. In some examples, the exam is automatically allocated to the first radiologist by the allocation manager 212 based on one or more rules defined by the rules creator 210 of FIG. 2. The allocated exam can be represented on a screen (e.g., a first and/or second screen 300, 400 of FIGS. 3 and 4) of the administrator user interface 202 by an exam identifier 302.

At blocks 804-808, the example method 800 includes identifying one or more characteristics associated with the allocated exam and/or the first radiologist. For example, at block 804, attributes associated with the allocated exam are identified. As mentioned above, exam attributes includes, for example, a modality, a body part under review, a priority level of the exam in view of patient criticality, and/or a service level agreement that specifies a time period for review of the exam in order to receive payment and/or a payment schedule. One or more of the aforementioned example exam attributes can be represented on a screen of the administrator user interface 202 by the exam attribute identifiers 304, 306, 308 (FIGS. 3 and 4).

At block 806, an availability status of the first radiologist is identified. For example, the availability of the first radiologist to review an exam can be represented on screens 300, 400 of the administrator user interface 202 by an examiner availability indicator 322. In some examples, if the first radiologist is accessing, for example, the radiology information system 106, the first radiologist is considered to be available for purposes of reviewing the allocated exam and the examiner availability indicator 322 will be highlighted. In other examples, the examiner availability indicator 322 reflects that the first radiologist is online but unavailable, working remotely, and/or offline.

In some examples, at block 806, the availability of the first radiologist identified at block 406 is selectively associated with a profile created using the profile creator 208 (FIG. 2). For example, the first radiologist can select a profile by interacting with the profile selector 408 (FIG. 4) and the first radiologist's availability, workload threshold, and/or workflow are based on the selected profile. The example method 800 includes considering the parameters defined by the selected profile in relation to allocation and/or assignment of the exam.

At block 808, the example method 800 includes identifying the radiologist's work queue. As described above, the first radiologist's examiner work queue 406 (FIG. 4) includes one or more exams previously assigned to and/or accepted by the first radiologist. In some examples, the example method 800 includes identifying the first radiologist's work queue in view of other radiologists' work queues. For example, block 808 includes identifying one or more metrics provided by the scorecard 316 (FIG. 3). An administrator can review the total number of assigned, allocated, and/or accepted exams for the first radiologist relative to other radiologists, as provided in the examiner summary viewer 318. Other metrics, such as priority levels and/or difficulty levels of exams allocated to the first radiologist, can also be considered.

In reviewing the radiologist work queue at block 808, the example method 800 includes identifying the first radiologist's history in accepting exams allocated and/or assigned to the first radiologist (block 810). The example method 800 at block 810 also includes identifying the first radiologist's history in initiating assignment of exams without allocation of the exam by the allocation manager 212. In some examples, the example method 800 at block 810 includes identifying historical patterns and trends of the first radiologist in, for example, rejecting assigned exams having certain attributes. The historical information identified at block 810 is based on, for example, the profile creator 208, the rules creator 210, the allocation manager 212, and/or the assignment manager 214 (FIG. 2).

The information concerning the allocated exam at block 802 and the exam characteristics associated with the allocated exam and/or the first radiologist of blocks 804-810 is stored in the database 216 of FIG. 2. Additionally, the information of blocks 802-810 can be selectively viewed via the examiner user interfaces 204a-n.

The example method 800 includes a decision whether to assign the allocated exam to the first radiologist (block 812). A decision whether to assign the allocated exam to the first radiologist can be based on the information related to the exam and/or the first radiologist identified at blocks 802-810. In considering the one or more factors of blocks 802-810, the example method 800 provides for review of exam distribution in view of load-balancing rules.

At block 814 of the example method 800, a decision is made to assign the allocated exam to the first radiologist. Assignment of the exam to the first radiologist is facilitated by the exam assignment tool 602 (FIG. 6) and implemented by the assignment manager 214 (FIG. 2). The exam identifier 302 associated with the assigned exam is displayed via the allocated/assigned exam summary 404 and/or the examiner work queue 406 associated with the first radiologist and displayed via, for example, the example second screen 400 (FIG. 4). Additionally, in some examples, the exam status identifiers 310, 312, 314 and/or the scorecard 316 are updated by the exam distributor 102 to reflect the assignment of the exam to the first radiologist's work queue. Also, in some examples, the administrator has reviewed the characteristics associated with the allocated exam and/or the first radiologist of blocks 804-810, but decides to assign the exam to the first radiologist in spite of one or more of the characteristics. For example, the administrator can assign the exam to the first radiologist even if the first radiologist is not currently available (e.g., is offline).

At block 816, the administrator has decided not to assign the allocated exam to the first radiologist. If the exam is not assigned to the radiologist to whom the allocation manager 212 allocated the exam, block 816 of the example method 800 involves identifying a second radiologist to review the exam. For example, the second radiologist can be identified based on availability of the second radiologist (block 818). In some examples, the second radiologist's availability is associated with profile created via the profile creator 208 (FIG. 2) and selected via the profile selector 408 (FIG. 4). In some examples, the second radiologist is identified based on the workload of the second radiologist (block 820). For example, if the second radiologist has a workload below a threshold defined by the rules creator 210 and/or if the second radiologist's work queue 406 is empty or only partially filled, the second radiologist is identified as a candidate to review the exam. Identification of the second radiologist as a candidate can be performed by the administrator and/or automatically by the exam distributor 102.

At block 822, the exam is assigned to the second radiologist. Assignment of the exam to the second radiologist is facilitated by the exam assignment tool 602 (FIG. 6) and implemented by the assignment manager 214 (FIG. 2). The exam identifier 320 associated with the assigned exam is displayed via the allocated/assigned exam summary 404 and/or the examiner work queue 406 associated with the second radiologist and displayed via, for example, the example second screen 400 (FIG. 4). Additionally, in some examples, the exam status identifiers 310, 312, 314 and/or the scorecard 316 are updated by the exam distributor 102 to reflect the assignment of the exam to the second radiologist's work queue. Additionally, because the exam has been assigned to the second radiologist, the exam is removed from the first examiner's allocated/assigned exam summary 404.

In operation, the example method 800 provides for an administrator to review automatic allocation of a medical exam to a first radiologist and facilitates a decision of the administrator to assign the allocated exam to the examiner in view of one or more properties associated with the first radiologist, the exam, and/or the distribution of exams across the network. Further, the example method 800 enables the administrator to assign the exam to a second radiologist based on the second radiologist's availability and/or workload. In such a manner, the example method 800 provides for management of exam distribution in view of load-balancing rules as well as user review of the application of the rules.

FIG. 9 illustrates a flow diagram of an example method 900 for accepting assignment of a medical exam. The example method 900 implements the exam distributor 102 of FIG. 2. In particular, the example method 900 depicts a method for accepting a medical exam assigned to a radiologist via the examiner user interface 202a of FIG. 2. The example method 900 begins at block 902 with updating the radiologist's availability status. As described above, when the radiologist accesses the radiology information system 106 (FIG. 1), the radiologist updates his/her availability status. The examiner availability indicator 322 visually represents the radiologist's online availability with respect to, for example, a local presence at a hospital or a remote presence.

In some examples, the radiologist is not presently accessing the radiology information system 106, but is working offline. In such examples, the examiner availability indicator 322 reflects that the radiologist is not available. In further examples, when the examiner accesses the radiology information system 106 and the radiologist's availability status is updated to reflect an online presence, the example method 900 include syncing the work the radiologist completed while offline with the radiology information system 106 (block 904). For example, if the radiologist started and/or completed review of one or more exams while working offline, the exam status indicators 310, 312, 314 update accordingly to reflect the current status of the exams.

At block 906, the example method 900 optionally includes selecting a radiologist profile. As described above, the radiologist can create one or more profiles via the profile creator 208. Allocation and/or assignment of exams to the radiologist is at least partially based on the properties of the profile with respect to radiologist availability and/or specialty. The example method 900 includes creating one or more profiles (block 908) and/or updating properties associated with one or more profiles (block 910). In selecting a radiologist profile at block 906, the radiologist can view exams allocated and/or assigned to the radiologist by the exam distributor 102 based on the criteria of the selected profile. In some examples, the radiologist profile is selected by the radiologist interacting with the profile selector 408 via one or more screens of the examiner user interface 204a. Information associated with one or more profiles is stored in the database 216 (FIG. 2).

At block 912, the example method 900 includes identifying one or more exams assigned to the radiologist by, for example, the assignment manager 214 based on, for example, the load-balancing rules defined by the rules creator 210. In some examples, the exam has been assigned to the examiner by an administrator as described with respect to the example method 800 of FIG. 8. An assigned exam is represented in the allocated/assigned exam summary 404 by the exam identifier 302 (FIG. 4). Information associated with one or more assigned exams is stored in the database 216.

At block 913 of the example method 900, implementation of the exam distributor 102 involves a decision whether to allow the radiologist to accept and/or reject an assigned exam. In some examples of the example method 900, the radiologist can only review assigned exams, update availability status, and/or create/update profiles without the option of accepting or rejecting an assigned exam. Such examples of the example method 900 can be implemented to prevent a radiologist from repeatedly accepting and/or rejecting exams having only certain exam attributes. If the radiologist is prevented from accepting and/or rejecting the assigned exam, according to, for example, one or more rules defined by the rules creator 210, the example method 900 restricts the radiologist to viewing the assigned exams as described at block 912. If the example method 900 provides for the option for the radiologist to accept and/or reject the assigned exam, the example method 900 proceeds to block 914.

At block 914, the example method 900 includes a decision whether to accept the assigned exam. For example, a radiologist can decide to accept or decline an assigned exam based on one or more factors, including, but not limited availability, specialty, and/or exam difficulty level. Acceptance or rejection of the exam is facilitated via the assignment tool 602 (FIG. 6). The exam distributor 102 stores information about the acceptance or rejection of the exam by the radiologist and/or characteristics of the accepted exam in the database 216 (FIG. 2) for use in future exam distributions.

If the radiologist decides to accept the exam, the example method 900 includes a decision by the radiologist at block 916 whether or not to review the exam at the present time (e.g., substantially immediately upon the exam being allocated to the radiologist and/or upon the radiologist accepting the exam).

In some examples, the radiologist is available to review exams and prefers to have the exam delivered for immediate review via the examiner interface 204a-n (e.g., the exam is opened via the exam reading tool 706 of FIG. 7) rather than first being delivered to the radiologist's work queue (e.g., the examiner work queue 406 of FIG. 4). In such examples, at block 918, the exam distributor 102 auto-serves the assigned exam to the radiologist such that the exam is presented for review substantially in real-time. In some examples of the example method 900, the radiologist can selectively decide to have exams successively delivered in auto-serve mode by the exam distributor 102. For example, after reviewing a first exam delivered in auto-serve mode, the exam distributor 102 auto-serves a second exam that has been assigned to the radiologist such that the radiologist's workflow progresses from reviewing the first exam to the second exam without the radiologist returning to the work queue to access the second exam. In such examples, identification of the assigned exams (e.g., block 912), acceptance of the assigned exams (e.g., block 914), and review of the exams (e.g., block 916) occurs without the radiologist leaving the exam reading tool 706 of the examiner interface 204a-n. In some examples, the exam status identifiers 310, 312, 314 and/or the scorecard 316 are updated by the exam distributor 102 to reflect the acceptance and review of the exam by the radiologist to inform, for example, an administrator and/or other radiologists in the network that the exam is a part of the radiologist's workload.

In other examples, the radiologist accepts an assigned exam, but chooses not to review the accepted exam at the present time. For example, the radiologist can review assigned exams as part of managing his/her workflow, but decide to review and report on the exam at a later time. In such examples, block 920 includes moving the accepted exam to the radiologist's work queue, where the exam identifier 322 associated with the accepted exam is displayed in the examiner work queue 406. Additionally, in some examples, the exam status identifiers 310, 312, 314 and/or the scorecard 316 are updated by the exam distributor 102 to reflect the assignment of the exam to the radiologist's work queue. In some examples, to review the exam at a later time, the radiologist returns to the examiner work queue 406 to selectively open the exam for review via the exam reading tool 706.

At block 922, the exam is rejected from review by the radiologist. Upon rejection of the exam by the radiologist, the exam is reallocated and/or reassigned by the allocation manager 212 and/or the assignment manager 214 in accordance with one or more rules defined by the rules creator 210 (FIG. 2). In other examples, one or more rules prevent the rejected exam from being reallocated to the radiologist. As described above, upon acceptance and/or rejection of the allocated exam, corresponding status information is provided to the administrator and/or the other radiologists of the network via respective user interfaces 202, 204n.

The example method 900 also provides for self-assignment of an exam to the radiologist's work queue. At block 924, the example method includes identifying exams that have not been allocated by the allocation manager 212 and/or assigned by the assignment manager 214. An unallocated exam is identified, for example, based on a status represented by one or more of the exam status identifiers 310, 312, 314. At block 926, the example method 900 includes a decision for a radiologist to assign the unallocated exam to his/her workload. If a decision is made to assign the unallocated exam to the radiologist, the example method 900 includes the decision whether to review the exam at the present time as described at block 916 with respect to acceptance of an assigned exam. For example, the radiologist can identify an unallocated exam, decide to assign the unallocated exam to himself, and then review the exam in real-time by having the exam distributor 102 auto-serve the exam such that the exam is opened for immediate review (e.g., block 918). In other examples, the radiologist selects to add the unallocated exam to his/her work queue (e.g., block 920). Assignment of the unallocated exam is facilitated by the assignment tool 602 accessed, for example, via the example first screen 300, which displays an overview of pending exams. Self-assignment of an exam at block 924 dynamically updates the status of the self-assigned exam as represented on the respective user interfaces 202, 204a-n accessed by the administrator and radiologists. If a decision is made not to self-assign an unallocated exam, the example method 900 ends.

In operation, the example method 900 provides for a radiologist to review exams assigned to the radiologist's work queue and facilitates acceptance and/or rejection of the assigned exams from the radiologist's work queue. Further, the example method 900 accommodates offline work by the radiologist by syncing the examiner's work and updating exam status accordingly when the radiologist accesses the radiology information system. The example method 900 provides for the radiologist to create and/or update profiles that at least partially control allocation and/or assignment of the exams. Further, the example method 900 provides for flexibility in either allowing a radiologist to accept or reject an assigned exam or limiting the radiologist to only reviewing exams in the radiologist's work queue to facilitate balanced distribution of exams. Implementation of the example method 900 also dynamically updates respective user interfaces viewed by other radiologists and/or administrators of the network to provide for collaborative, interactive workflow management.

The example method 900 also provides for flexibility in delivering an exam that has been distributed to the radiologist based on the load-balancing rules. A radiologist can select to review the exam immediately or substantially immediately upon the exam being allocated and/or assigned to the radiologist via auto-serve mode. Auto-serve mode provides for the radiologist to maximum his/her time by successively delivering exams to the radiologist via an exam reading screen of the examiner interface, without requiring the radiologist to switch between the examiner work queue and the exam reading screen to retrieve assigned exams. However, the example method 900 also provides for the radiologist to save the exam to the examiner work queue where the exam can be identified as part of the radiologist's workload and retrieved for review at a later time. Such examples provide for the radiologist to view the exam in the radiologist's work queue as part of workload management. The radiologist can evaluate the exam's priority in view of other exams contained in the radiologist's work queue.

Thus, the example method 900 provides for an efficiency-driven approach to exam assignment and review by accommodating for radiologist workflow preferences.

Figure 10:
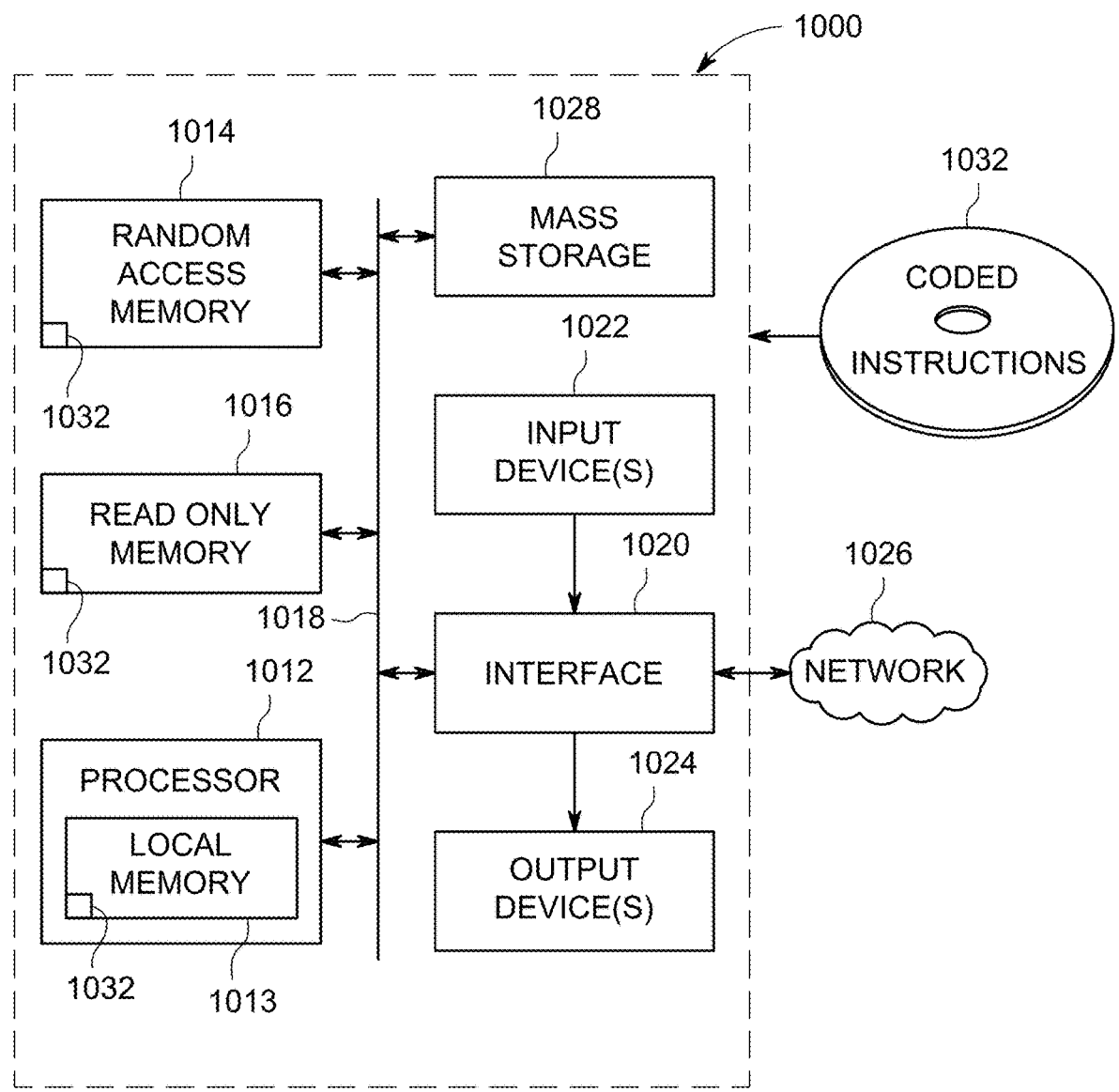
FIG. 10 shows a block diagram of an example processor system that may be used to implement systems and methods described herein.

FIG. 10 is a block diagram of an example processor platform 1000 capable of executing the instructions of FIGS. 7 and 8 to implement the exam distributor 102 of FIG. 2. The processor platform 1000 can be, for example, a server, a personal computer, a mobile device (e.g., a cell phone, a smart phone, a tablet such as an IPAD™), a personal digital assistant (PDA), an Internet appliance, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 can be implemented by flash memory and/or any other desired type of memory device. Access to the main memory 1014, 1016 is controlled by a memory controller.

The processor platform 1000 of the illustrated example also includes an interface circuit 1020. The interface circuit 1020 can be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1020 of the illustrated example, thus, typically includes a graphics driver card, a graphics driver chip or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIGS. 7 and 8 can be stored in the mass storage device 1028, in the volatile memory 1014, in the non-volatile memory 1016, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A system comprising a processor, the processor configured to implement:
    an exam distributor to:
        assign a first medical exam to a first examiner based on a workload availability threshold for the examiner and an examiner availability indicator for the first examiner wherein the examiner availability indicator represents an online presence of the first examiner that indicates whether the first examiner is accessing a radiology information system;
        deliver the first medical exam to one of a reading tool to be displayed via a first graphical user interface or an examiner work queue to be displayed via a second graphical user interface, the first graphical user interface and the second graphical user interface to be viewed by the first examiner;
        receive, via a third graphical interface, a first user input including a first adjustment to the workload availability threshold for the first examiner based on the delivery of the first exam to the reading tool or the examiner work queue, the third graphical interface to be viewed by a second examiner;
        automatically adjust a workload availability threshold for a third examiner based on the first adjustment;
        assign a second medical exam to the first examiner or the third examiner based on the respective adjusted work availability thresholds for the first examiner and the third examiner; and
        auto-serve one or more additional medical exams to the first examiner or the third examiner based on at least one load balancing rule, wherein the auto-serve is adjusted based at least in part on a review efficiency of the first examiner and the third examiner.

2. The system of claim 1, wherein the exam distributor is to receive a second user input including one of an acceptance of the first medical exam by the first examiner or a rejection of the first medical exam by the first examiner, the exam distributor to further assign the second medical exam to the first examiner or the third examiner based on the second user input.

3. The system of claim 1, wherein the exam distributor is to assign the second medical exam to the third examiner based on an examiner availability indicator for the third examiner.

4. The system of claim 1, wherein the exam distributor is to update the workload availability threshold for the first examiner based on the delivery of the first medical exam to the reading tool or the examiner work queue.

5. The system of claim 1, wherein the exam distributor is to deliver the first medical exam to the reading tool or the examiner work queue based on a priority level of the first medical exam.

6. The system of claim 1, wherein the exam distributor is to update a workload availability indicator for the first examiner based on the delivery of the first medical exam to the reading tool or the examiner work queue, the workload availability indicator to be viewed via the first graphical user interface and the third graphical user interface.

7. The system of claim 1, wherein the first adjustment is to one of increase the workload availability threshold for the first examiner or decrease the workload availability threshold for the first examiner.

8. The system of claim 1, wherein the exam distributor is to deliver the exam to the reading tool or the examiner work queue based on a second user input received via one of the first graphical user interface or the second graphical user interface.

9. The system of claim 8, wherein if the second user input indicates the first medical exam is to be delivered to the reading tool, the exam distributor is to display the first medical exam and wherein if the second user input indicates the first medical exam is to be delivered to the examiner work queue, the exam distributor is to generate an exam identifier for the first medical exam and display the exam identifier in the examiner work queue.

10. A method comprising:
    assigning, by executing an instruction with a processor, a first medical exam to a first examiner based on a workload availability threshold for the examiner and an examiner availability indicator for the first examiner, wherein the examiner availability indicator represents an online presence of the first examiner that indicates whether the first examiner is accessing a radiology information system;
    delivering, by executing an instruction with the processor, the first medical exam to one of a reading tool to be displayed via a first graphical user interface or an examiner work queue to be displayed via a second graphical user interface, the first graphical user interface and the second graphical user interface to be viewed by the first examiner;
    receiving, via a third graphical interface, a first user input including a first adjustment to the workload availability threshold for the first examiner based on the delivery of the first exam to the reading tool or the examiner work queue, the third graphical interface to be viewed by a second examiner;
    automatically adjusting, by executing an instruction with the processor, a workload availability threshold for a third examiner based on the first adjustment;
    assigning, by executing an instruction with the processor, a second medical exam to the first examiner or the third examiner based on the respective adjusted work availability thresholds for the first examiner and the third examiner; and
    auto-serving one or more additional medical exams to the first examiner or the third examiner based on at least one load balancing rule, wherein the auto-serve is adjusted based at least in part on a review efficiency of the first examiner and the third examiner.

11. The method of claim 10, further including updating the workload availability threshold for the first examiner based on the delivery of the first medical exam to the reading tool or the examiner work queue.

12. The method of claim 10, wherein the delivering of the first medical exam to the reading tool or the examiner work queue is based on a priority level of the first medical exam.

13. The method of claim 10, further including updating a workload availability indicator for the first examiner based on the delivery of the first medical exam to the reading tool or the examiner work queue, the workload availability indicator to be viewed via the first graphical user interface and the third graphical user interface.

14. The method of claim 10, further including:
receiving a second user input including one of an acceptance of the first medical exam by the first examiner or a rejection of the first medical exam by the first examiner;
performing a comparison of the second user input to a third user input including one of an acceptance of a third exam or a rejection of the third medical exam, the third user input to be received prior to the receipt of the second user input; and
generating an exam acceptance trend for the first examiner based on the comparison.

15. A non-transitory computer readable storage medium comprising instructions that, when executed, cause a machine to at least:
assign a first medical exam to a first examiner based on a workload availability threshold for the examiner and an examiner availability indicator for the first examiner, wherein the examiner availability indicator represents an online presence of the first examiner that indicates whether the first examiner is accessing a radiology information system;
deliver the first medical exam to one of a reading tool to be displayed via a first graphical user interface or an examiner work queue to be displayed via a second graphical user interface, the first graphical user interface and the second graphical user interface to be viewed by the first examiner;
receive, via a third graphical interface, a first user input including a first adjustment to the workload availability threshold for the first examiner based on the delivery of the first exam to the reading tool or the examiner work queue, the third graphical interface to be viewed by a second examiner;
automatically adjust a workload availability threshold for a third examiner based on the first adjustment;
assign a second medical exam to the first examiner or the third examiner based on the respective adjusted work availability thresholds for the first examiner and the third examiner; and
auto-serve one or more additional medical exams to the first examiner or the third examiner based on at least one load balancing rule, wherein the auto-serve is adjusted based at least in part on a review efficiency of the first examiner and the third examiner.

16. The non-transitory computer readable storage medium of claim 15, wherein the instructions further cause the machine to update the workload availability threshold for the first examiner based on the delivery of the first medical exam to the reading tool or the examiner work queue.

17. The non-transitory computer readable storage medium of claim 15, wherein the instructions further cause the machine to deliver the first medical exam to the reading tool or the examiner work queue based on a priority level of the first medical exam.

* * * * *